United States Patent
Wang et al.

(10) Patent No.: US 6,620,813 B1
(45) Date of Patent: Sep. 16, 2003

(54) HYDROXAMATE DERIVATIVES OF NON-STEROIDAL ANTI-INFLAMMATORY DRUGS

(75) Inventors: Tingmin Wang, San Marcos, CA (US); Ching-San Lai, Carlsbad, CA (US)

(73) Assignee: Medinox, Inc., San Diego, CA (US)

( * ) Notice: Subject to any disclaimer, the term of this patent is extended or adjusted under 35 U.S.C. 154(b) by 0 days.

(21) Appl. No.: 10/177,683

(22) Filed: Jun. 21, 2002

(51) Int. Cl.$^7$ .................. A61K 31/53; A61K 31/425; C07D 253/08; C07C 229/60; C07C 69/76

(52) U.S. Cl. .................. 514/243; 514/369; 514/420; 514/507; 514/602; 514/603; 514/604; 514/605; 544/183; 548/182; 548/207; 560/38; 560/56

(58) Field of Search ..................... 514/243, 369, 514/420, 507, 602, 603, 604, 605; 544/183; 548/182, 507; 560/38, 56

(56) References Cited

U.S. PATENT DOCUMENTS

| | | | |
|---|---|---|---|
| 4,160,452 A | | 7/1979 | Theeuwen .................. 128/260 |
| 4,206,220 A | * | 6/1980 | Sloan |
| 4,256,108 A | | 3/1981 | Theeuwen .................. 128/260 |
| 4,265,874 A | | 5/1981 | Bonsen et al. ............... 424/15 |
| 5,516,789 A | * | 5/1996 | Brooks et al. |

OTHER PUBLICATIONS

Onoe et al., "IL–13 and IL–14 inhibit bone resorption by supressing cyclooxygenase–2–dependent prostaglandin synthesis in osteoblasts," Biochem. Pharma., 55:758–764, 1996.

Piazza et al., "apoptosis primarily accounts for the growth–inhibitory properties of sulindac metabolites and involves a mechanism that is independent of cyclooxygen inhibition, cell cycle arrest and p53 induction," Cancer Research, 57: 2452–2459, 1997.

Qiao et al., "Effect of aspirin on induction of apoptosis in HT–29 human colon adenocarcinoma cells," Biochemical Pharmacology, 55: 53–64, 1998.

Richard et al., "Dibenzoxepinone hydroxylamines and hydroxamic acids: dual inhibitors of cyclooxygenase and 5–lipoxygenase with potent topical antiinflammatory activity," J.Med.Chem., 39: 246–252, 1996.

Shiff et al., "Nonsteroidal antiinflammatory drugs inhibit the proliferation of colon adenocarcinoma cells: effects on cell cycle and apoptosis," Experimental Cell Research, 222: 179–188, 1996.

Sirois, "Pharmacology of the Leukotrienes," *Advances in Lipid Research*, vol. 21, Orlando: Academic Press, 1985, p. 79–101.

Slater et al., "Expression of cyclooxygenase types 1 and 2 in human fetal membranes at term," Am.J.Obstet.Gynecol., 172: 77–82, 1995.

(List continued on next page.)

*Primary Examiner*—Johann Richter
*Assistant Examiner*—Paul A. Zucker
(74) *Attorney, Agent, or Firm*—Stephen E. Reiter; Foley & Lardner

(57) ABSTRACT

In accordance with the present invention, there are provided novel chemical entities which have multiple utilities, e.g., as prodrugs of NSAIDs; as dual inhibitors of cyclooxygenase (COX) and 5-lipoxygenase (5-LO); as anticancer agents (through promoting apoptosis and/or inhibiting the matrix metalloproteinases (MMPs)), and the like. Invention compounds comprise a non-steroidal anti-inflammatory agent (NSAID), covalently linked to a hydroxamate. Invention compounds are useful for a variety of applications, such as, for example, treating inflammation and inflammation-related conditions; reducing the side effects associated with administration of anti-inflammatory agents; promoting apoptosis; inhibiting matrix metalloproteinases; and the like.

36 Claims, 3 Drawing Sheets

OTHER PUBLICATIONS

Soll et al., "Nonsteroidal anti–inflammatory drugs and peptic ulcer disease," Ann.Internal Medicine, 114: 307–319, 1991.

Stewart et al., "Structure–activity relationsips of N–hydroxyurea 5–lipoxygenase inhibitors," J.Med.Chem., 40: 1955–1968, 1997.

Summers et al., "Hydroxamic acid inhibitors of 5–lipoxygenase: quantitative structure–activity relationships," J.Med.Chem., 33:992–998, 1990.

Unangst et al., Synthesis and Biological evaluation of 5–{{3,5–Bis(1,1–dimethylethyl)–4–hydroxyphenyl]methylene]oxazoles, –thiazoles, and –imidazoles: novel dual 5–lipoxygenase and cyclooxygenase inhibitors with.

Wallace, "Nonsteroidal anti–inflammatory drugs and gastroenteropathy: the second hundred years," Gastroenterology, 112: 1000–1016, 1997.

Whittaker et al., "Design and therapeutic application of matrix metalloproteinase inhibitors," Chem. Rev., 99: 2735–2776, 1999.

Wong et al., "Antiarthritic profile of BF–389—A novel anti–inflammatory agent with low ulcerogenic liability," Agents Actions, 37:90–98, 1992.

Cheng et al., "Design and synthesis of piperazine–based matrix metalloproteinase inhibitors," J.Med.Chem., 43: 369–380, 2000.

Cheng et al., "Role of proostacyclin in the cardiovascular response to thromoxane A2," Science, 296: 539–541, 2002.

Glaser et al., "Etodolac selectively inhibits human prostaglandin G/H synthase 2 (PGHS–2) versus human PGHS–1," European Journal of Pharmacology, 281: 107–111, 1995.

Graham et al., "Nonsterodial anti–inflammatory effect of sulindac sulfoxide and sulfide on gastric mucosa," Clin. Pharmecol. Ther., 38: 65–70, 1985.

Hial et al., "Antiproliferative activity of anti–inflammatory drugs in two mammalian cell culture lines," Journal of Pharm. and Experiment Therapeutics, 202: 446–454, 1997.

Hidaka et al., "Pharmacological properties of a new anti–inflammatory compound . . . ," Japan J. Pharmacology, 36: 77–86, 1984.

Hubbard et al., "Inhibition of growth and linoleate–enhanced metastasis of a transplantable mouse mammary tumor by indomethacin," Cancer Letters, 43: 111–120, 1988.

Ikuta et al., "Snythesis and antiflammatory activities of 3–(3, 5–Di–tert–butyl–4–hydroxybenylidene)pyrrolidin–2–ones," J.Med.Chem., 30:1995–1998, 1987.

Inagaki et al., "Novel antiarthritic agents with 1,2–isothiazolidine–1, 1–dioxide (y–sultam) skeleton: Cytokine suppressive dual inhibitors of cyclooxygenase–2 and 5–lipoxygenase," J.Med.Chem., 43: 2040–2048, 2000.

Kaplan–Machlis et al., "The Cyclooxygenase–2 inhibitors: safety and effectiveness," The Annals of Pharmacotherapy, 33: 979–88, 1999.

Kargman et al., "Characterization of prostaglandin G/H synthase 1 and 2 in rat, dog, monkey, and human gastrointestinal tracts," Gastroenterology, 111: 445–454, 1996.

Kolasa et al., "Nonsteroidal anti–inflammatory drugs as scaffolds for the design of 5–lipoxygenase inhibitors," J.Med.Chem., 40:819–824, 1997.

Lundholm et al., "Anti–inflammatory treatment may prolong survival in undernourished patients with metastatic solid tumors," Cancer Research, 54:5602–5606, 1994.

Mahmoud et al., "The sulfide metabolite of sulindac prevents tumors and restores enterocyte apoptosis in a murine model of familial adenomaaatous polyposis," Carcinogenesis, 19: 87–91, 1998.

Meade et al., "Differential inhibition of prostaglandin endoperoxide synthase (cyclooxygenase) isozymes by aspirin and other non–steroidal anti–inflammatory drugs," Journal of Biological Chemistry, 268: 6610–6614, 1993.

Mitchell et al., "Selectivity of nonsteroidal antiinflammatory drugs as inhibitors of constitutive and inducible cyclooxygenase," Proc. Natl. Acad. Sci. USA, 90: 11693–11697, 1993.

Barlaam et al., "New a–Substituted succinate–based hydroxamic acids as TNFa convertase inhibitors," J.Med.Chem., 42: 4890–4908, 1999.

Bayer et al., "Arrest of cultured cells in the G1 phase of the cell cycle by indomethacin," Journal of Pharmacology and Experimental Therapeutics, 210: 106–111, 1979.

Bayer et al., "Evidence that indomethacin reversibly inhibits cell growth in the G1 phase of the cell cycle," Biochmical Pharm., 28: 441–443, 1979.

Bellosillo et al., "Aspirin and salicylate induce apoptosis and activation of caspases in B–cell chronic lymphocytic leukemia cells," Blood, 92: 1406,1414, 1998.

Bjarnason et al., "Side effects of nonsteroidal anti–inflammatory drugs on the small and large intestine in humans," Gastroenterology, 104: 1832–1847, 1993.

Carson et al., "The Relative gastrointestinal toxicity of the nonsteroidal anti–inflammatory drugs," Arch. Internal Medicine, 147: 1054–1059, 1987.

* cited by examiner

HYDROXAMATE DERIVATIVES OF NON-STEROIDAL ANTI-INFLAMMATORY DRUGS

FIELD OF THE INVENTION

The present invention relates to hydroxamate derivatives of non-steroidal anti-inflammatory drugs (NSAIDs). Invention compounds have multiple uses, for example, as prodrugs of NSAIDs, dual inhibitors of cyclooxygenase (COX) and 5-lipoxygenase (5-LO), as anticancer agents (through promoting apoptosis and/or inhibiting matrix metalloproteinase enzymes (MMP)), and the like. In another aspect, the present invention relates to formulations containing invention compounds and methods for use thereof.

BACKGROUND OF THE INVENTION

A. NSAIDs

Despite the advent of modem pharmaceutical technology, many drugs still possess untoward toxicities which often limit the therapeutic potential thereof. For example, although non-steroid anti-inflammatory drugs (NSAIDs) are a class of compounds which are widely used for the treatment of inflammation, pain and fever, NSAIDs (e.g., naproxen, aspirin, ibuprofen and ketoprofen) can cause gastrointestinal ulcers, a side-effect that remains the major limitation to the use of NSAIDs (see, for example, J. L. Wallace, in Gastroenterol. 112:1000–1016 (1997); A. H. Soll et al., in Ann Intern Med. 114:307–319 (1991); and J. Bjarnason et al., in Gastroenterol. 104:1832–1847 (1993)).

There are two major ulcerogenic effects of NSAIDs: (1) irritant effects on the epithelium of the gastrointestinal tract and (2) suppression of gastrointestinal prostaglandin synthesis. In recent years, numerous strategies have been attempted to design and develop new NSAIDs that reduce the damage to the gastrointestinal tract. These efforts, however, have largely been unsuccessful. For example, enteric coating or slow-release formulations designed to reduce the topical irritant properties of NSAIDs have been shown to be ineffective in terms of reducing the incidence of clinically significant side effects, including perforation and bleeding (see, for example, D. Y. Graham et al., in Clin. Pharmacol. Ther. 38:65–70 (1985); and J. L. Carson, et al., in Arch. Intern. Med., 147:1054–1059 (1987)).

It is well recognized that aspirin and other NSAIDs exert their pharmacological effects through the non-selective inhibition of cyclooxygenase (COX) enzymes, thereby blocking prostaglandin synthesis (see, for example, J. R. Van in Nature, 231:232–235 (1971)). There are two types of COX enzymes, namely COX-1 and COX-2. COX-1 is expressed constitutively in many tissues, including the stomach, kidney, and platelets, whereas COX-2 is expressed only at the site of inflammation (see, for example, S. Kargan et al. in Gastroenterol., 111:445–454 (1996)). The prostaglandins whose production is mediated by COX-1 are responsible for many of their physiological effects, including maintenance of gastric mucosal integrity.

Many attempts have been made to develop NSAIDs that only inhibit COX-2, without impacting the activity of COX-1 (see, for example, J. A. Mitchell et al., in Proc. Natl. Acad. Sci. USA 90:11693–11697 (1993); and E. A. Meade et al., in J. Biol. Chem., 268:6610–6614 (1993)). There are several NSAIDs presently on the market (e.g., rofecoxib and celecoxib) that show marked selectivity for COX-2 (see, for example, E. A. Meade, supra.; K. Glaser et al., in Eur. J. Pharmacol. 281:107–111 (1995) and Kaplan-Machlis, B., and Klostermeyer, B S in Ann Pharmacother. 33:979–88, (1999)). These drugs appear to have reduced gastrointestinal toxicity relative to other NSAIDs on the market.

On the basis of encouraging clinical as well as experimental data, the development of highly selective COX-2 inhibitors appears to be a sound strategy to develop a new generation of anti-inflammatory drugs. However, the physiological functions of COX-1 and COX-2 are not always well defined. Thus, there is a possibility that prostagladins produced as a result of COX-1 expression may also contribute to inflammation, pain and fever. On the other hand, prostagladins produced as a result of COX-2 expression have been shown to play important physiological functions, including the initiation and maintenance of labor and in the regulation of bone resorption (see, for example, D. M. Slater et al., in Am. J. Obstet. Gynecol., 172:77–82 (1995); and Y. Onoe et al., in J. Immunol. 156:758–764 (1996)), thus inhibition of this pathway may not always be beneficial. Considering these points, highly selective COX-2 inhibitors may produce additional side effects above and beyond those observed with standard NSAIDs, therefore such inhibitors may not be highly desirable.

Indeed, recent studies with first generation COX-2 inhibitors reveal that arthritic patients treated with rofecoxib had a five-fold higher risk of heart attack, compared to patients treated with naproxen (Wall St. Jrnl, 5/1/10). Thus, like aspirin, naproxen appears to exert cardioprotective effects, while selective COX-2 inhibitors do not. The reason why selective COX-2 inhibitors appear to cause elevated risk of heart attack has been studied (see Y. Cheng et al., in Science 296(19): 539–541 (2002)). Because of this potentially serious side effect of selective COX-2 inhibitors, there is still a need in the art for new NSAIDs (or derivatives thereof) with reduced gastrointestinal (GI) side effects.

B. Dual Inhibitors of Cyclooxygenase (COX) and 5-Lipoxygenase (5-LO)

The enzyme 5-LO is an iron-containing dioxygenase (see M. Gibian et al., in Bio-Org. Chem. 1:117 (1977)) that catalyzes the first step of the biochemical pathway to convert arachidonic acid to leukotrienes. Leukotrienes are important mediators in inflammatory diseases including asthma, arthritis, psoriasis and allergy (see P, Sirois in Adv. Lipid Res. 21:79 (1995)). Inhibition of 5-LO is an important avenue for therapeutic treatment of these diseases.

Hydroxamates are well known to form strong complexes with transition metal ions including iron (see H. Kiehl in The Chemistry And Biochemistry Of Hydroxyamic Acids, Karger, Basel (1982)). Some hydroxamates have shown good inhibitory activity against 5-LO (See, for example, J. B. Summers et al., in J. Med. Chem. 33:992–998(1990); A. O. Stewart et al., in J. Med. Chem. 40: 1955–1968 (1997); and T. Kolasa et al., in J. Med. Chem. 40:819–824 (1997)).

As described above, NSAIDs are relatively non-specific COX inhibitors, that commonly cause adverse effects, especially, gastrointestinal ulceration. A compound which provides inhibitory activities against both COX and 5-LO may provide improved anti-inflammatory activity with reduced NSAID-related side effects. Indeed, several research groups have studied dual inhibitors containing an hydroxamic acid group in their molecules (see T. Hidaka et al., in Jpn. L. Pharmacol, 36: 77–85 (1984); H. Ikuta et al., in J. Med. Chem. 30:1995–1998 (1987); S. Wong et al., in Agents Actions 37:90–98(1992); P. C. Unangst et al., in J. Med. Chem. 37: 322–328 (1994); R. Richard L. et al., in J. Med. Chem. 39:246–252 (1996); and M. Inagak et al., in J.

Med. Chem. 43:2040–2048 (2000)). In those studies, the molecule as an intact entity is designed to provide inhibitory activity against both COX and 5-LO. In general, however, these approaches have not proven to be very effective.

Accordingly, there remains a need in the art for compounds which are more effective for the treatment of various inflammatory diseases with reduced NSAID-related side effects.

C. Anticancer Drugs

From experimental models of carcinogenesis, it has become apparent that NSAIDs have cancer chemopreventive properties, although their application to human cancer and the extent of their benefits in the clinic is presently a matter of intensive investigation (see G. A. Piazza et al., in Cancer Research, 57: 2452–2459 (1997)). While the results have been explained by reference to different mechanisms, many experiments have shown that NSAIDs have the potential to induce apoptosis (see, for example, K. Lundholm et al., in Cancer Research 54:5602–5606(1994); B. M. Bayer et al., in Biochem. Pharma. 28:441–443(1979), and in The J. Pharma. And Experiment. Therapeutics 210:106 (1979); N. N. Mahmoud et al., in Carcinogenesis 19:876–91(1998); V. Hial et al., in The J. Pharma. And Experiment. Therapeutics 202:446–454 (1977); B. Bellosillo et al., in Blood 92: 1406–1414(1998); N. E. Hubbard et al., in Cancer letters 43:111–120(1988); L. Qiao et al., in Biochem. Pharma. 55:53–64(1998); and S. J. Shiff et al., in Experimental Cell Res. 222: 179–188(1996)).

Matrix metalloproteinases (MMPs), also called matrixines, are a family of structurally related zinc-containing enzymes that mediate the breakdown of connective tissue and are therefore targets for therapeutic inhibitors in many inflammatory, malignant and degenerative diseases (see M. Whittaker et al., in Chem. Rev. 99: 2735–2776 (1999)). Consequently a considerable amount of effort has been invested in designing orally active MMP inhibitors with the expectation that such agents will be able to either halt or slow the progression of diseases such as osteoarthritis, tumor metastasis, and corneal ulceration (see M. Cheng et al., 43: 369–380 (2000)). Since hydroxamate can form strong complexes with transition state metal ions including zinc, the vast majority of MMP inhibitors incorporate an hydroxamate group as the zinc binding ligand (see M. Whittaker et al., in Chem. Rev. 99: 2735–2776 (1999); B. Barlaam et al., 42:4890–4908(1999)).

Accordingly, incorporation of the hydroxamate functionality into pharmacologically active compounds may provide novel compounds with enhanced anti-cancer activity and/or a reduced side effect profile.

SUMMARY OF THE INVENTION

In accordance with the present invention, there are provided novel chemical entities which have multiple utilities, e.g., as prodrugs of NSAIDs; as dual inhibitors of cyclooxygenase (COX) and 5-lipoxygenase (5-LO); as anticancer agents (through promoting apoptosis and/or inhibiting matrix metalloproteinases (MMPs), and the like. Invention compounds comprise a non steroidal anti-inflammatory agent (NSAID), covalently linked via a suitable linker, to a hydroxamate. Invention compounds are useful for a variety of applications, such as, for example, treating inflammation and inflammation-related conditions; enhancing anti-inflammatory activity of NSAIDs, reducing the side effects associated with administration of anti-inflammatory agents; as anticancer agents (through promoting apoptosis and/or inhibiting matrix metalloproteinases (MMPs)), and the like.

Invention compounds are conjugate compounds of NSAIDs and hydroxamates, covalently linked in such a way that they can be broken into two individual molecules in the circulation system to provide their own inhibitory activity against COX and 5-LO, respectively.

The NSAID component of invention compounds is capable of inducing apoptosis and the hydroxamate component is capable of inhibiting MMP. The two components are simultaneously administered as they are covalently linked, which in due course produces the original two components upon exposure to enzyme(s) in the circulatory system. Upon cleavage, the individual components are capable of contributing their cancer preventive activity with reduced NSAID-related side effects.

DETAILED DESCRIPTION OF THE INVENTION

Figure 1:
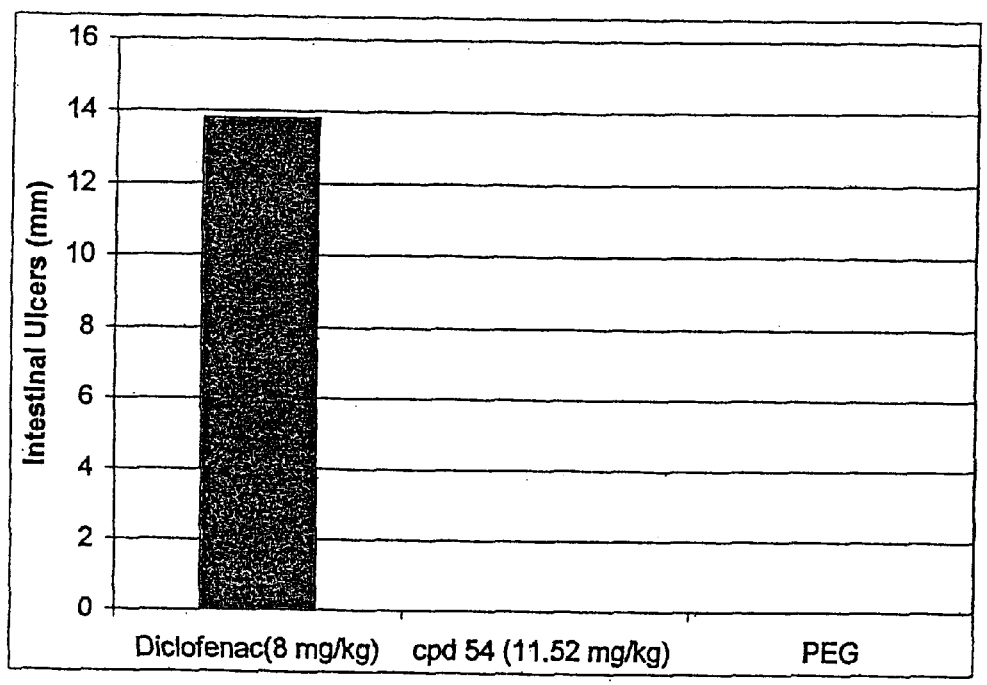
FIG. 1 illustrates the total length of intestinal ulcers measured for rats treated with vehicle, diclofenac or equimolar invention compound 54.

In accordance with the present invention, there are provided compounds having the structure:

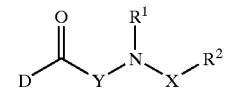

wherein:

X is $C(O)$, $C(O)O$, $S(O)$, $S(O)_2$, $C(S)$, $C(O)S$, $C(S)S$, $C(S)O$, and the like;

Y is O or S;

$R^1$ and $R^2$ are each independently hydrogen, hydrocarbyl, substituted hydrocarbyl, alkoxy, substituted alkoxy, aryloxy, substituted aryloxy, heterocyclic, or substituted heterocyclic; or $R^1$ and $R^2$ together with N and X can form a cyclic moiety; and D—C(O)— is derived from a non-steroidal anti-inflammatory drug (NSAID) bearing a free carboxyl group.

In a presently preferred embodiment of the invention, X is $C(O)$ or $S(O)_2$ and Y is O.

In another presently preferred embodiment of the present invention, $R^1$ and $R^2$ are each independently alkyl, substituted alkyl, aryl, substituted aryl, alkoxy, or substituted alkoxy. Substituents on $R^1$ and/or $R^2$, when optionally present, include optionally substituted alkyl, optionally substituted cycloalkyl, optionally substituted heterocyclic, optionally substituted aryl, optionally substituted heteroaryl, optionally substituted aryloxy, optionally substituted alkoxy, thioalkyl, hydroxyl, mercapto, alkylthio, alkylthioalkyl, halogen, trihalomethyl, cyano, nitro, nitrone, —C(O)H, carboxyl, alkoxycarbonyl, carbamate, sulfonyl, alkylsulfonyl, alkylsulfonylalkyl, sulfinyl, alkylsulfinyl, alkylsulfinylalkyl, sulfonamide, sulfuryl, amino, alkylamino, arylamino, aminosulfonyl, alkylaminosulfonyl, dialkylaminosulfonyl, amido, acyl, oxyacyl, —$SO_3M$ wherein M is $H^+$, $Li^+$, $Na^+$, $K^+$, $NH_4^+$, and the like, or —$PO_3M$ wherein M is $H^+$, $Li^+$, $Na^+$, $K^+$, $NH_4^+$, and the like; or —$OC(S)NR^3$, —$OC(O)NR^3$, —$C(S)NR^3$, —$NR^3C(S)R^3$, —$NR^3C(S)NR_3$, —$OC(S)NR^3$, —$NR^3C(S)OR^3$, —$C(S)OR^3$, —$OC(S)R^3$, —$OC(S)OR^3$, and the like, wherein $R^3$ is independently any of the substituents contemplated for $R^1$ and $R^2$ as defined herein.

NSAIDs contemplated for incorporation into invention compounds include aspirin (i.e., acetylsalicylic acid), diclofenac, naproxen, indomethacine, flubiprofen, sulindac, ibuprofen, benoxaprofen, benzofenac, bucloxic acid, butibufen, carprofen, cicloprofen, cinmetacin, clidenac, clopirac, etodolac, fenbufen, fenclofenac, fenclorac, fenoprofen, fentiazac, flunoxaprofen, furaprofen, furobufen, furafenac, ibufenac, indoprofen, isoxepac, ketoprofen, lonazolac, metiazinic, mefenamic acid, meclofenmic acid, piromidic acid, salsalate, miroprofen, oxaprozin, oxepinac, pirprofen, pirozolac, protizinic acid, suprofen, tiaprofenic acid, tolmetin, zomepirac, and the like.

As employed herein, "hydrocarbyl" comprises any organic radical wherein the backbone thereof comprises carbon and hydrogen only. Thus, hydrocarbyl embraces alkyl, cycloalkyl, alkenyl, cycloalkenyl, alkynyl, aryl, alkylaryl, arylalkyl, arylalkenyl, alkenylaryl, arylalkynyl, alkynylaryl, and the like.

As employed herein, "substituted hydrocarbyl" comprises any of the above-referenced hydrocarbyl groups further bearing one or more substituents selected from hydroxy, alkoxy (of a lower alkyl group), mercapto (of a lower alkyl group), cycloalkyl, substituted cycloalkyl, heterocyclic, substituted heterocyclic, aryl, substituted aryl, heteroaryl, substituted heteroaryl, aryloxy, substituted aryloxy, halogen, trifluoromethyl, cyano, nitro, nitrone, amino, amido, —C(O)H, acyl, oxyacyl, carboxyl, carbamate, dithiocarbamoyl, sulfonyl, sulfonamide, sulfuryl, and the like.

As employed herein, "alkyl" refers to saturated straight or branched chain hydrocarbon radical having in the range of 1 up to about 20 carbon atoms. "Lower alkyl" refers to alkyl groups having in the range of 1 up to about 5 carbon atoms. "Substituted alkyl" refers to alkyl groups further bearing one or more substituents as set forth above.

As employed herein, "alkoxy" refers to —O-alkyl groups having in the range of 2 up to 20 carbon atoms and "substituted alkoxy" refers to alkoxy groups further bearing one or more substituents as set forth above.

As employed herein, "cycloalkyl" refers to a cyclic ring-containing groups containing in the range of about 3 up to about 8 carbon atoms, and "substituted cycloalkyl" refers to cycloalkyl groups further bearing one or more substituents as set forth above.

As employed herein, "cycloalkylene" refers to divalent ring-containing groups containing in the range of about 3 up to about 8 carbon atoms, and "substituted cycloalkylene" refers to cycloalkylene groups fuirther bearing one or more substituents as set forth above.

As employed herein, "alkylene" refers to saturated, divalent straight or branched chain hydrocarbyl groups typically having in the range of about 2 up to about 12 carbon atoms, and "substituted alkylene" refers to alkylene groups further bearing one or more substituents as set forth above.

As employed herein, "oxyalkylene" refers to saturated, divalent straight or branched chain oxygen-containing hydrocarbon radicals typically having in the range of about 2 up to about 12 carbon atoms, and "substituted oxyalkylene" refers to oxyalkylene groups further bearing one or many substituents as set forth above.

As employed herein, "alkenyl" refers to straight or branched chain hydrocarbyl groups having at least one carboncarbon double bond, and having in the range of about 2 up to 12 carbon atoms, and "substituted alkenyl" refers to alkenyl groups further bearing one or more substituents as set forth above.

As employed herein, "cycloalkenyl" refers to cyclic ring-containing groups containing in the range of 3 up to 20 carbon atoms and having at least one carbon-carbon double bond, and "substituted cycloalkenyl" refers to cycloalkenyl groups further bearing one or more substitutents as set forth above.

As employed herein, "alkenylene" refers to divalent straight or branched chain hydrocarbyl groups having at least one carbon-carbon double bond, and typically having in the range of about 1 up to 12 carbon atoms, and "substituted alkenylene" refers to alkenylene groups further bearing one or more substituents as set forth above.

As employed herein, "alkenylene" refers to divalent straight or branched chain hydrocarbyl groups having at least one carbon—carbon double bond, and typically having in the range of about 2 up to 12 carbon atoms, and "substituted alkenylene" refers to alkenylene groups further bearing one or more substituents as set forth above.

As employed herein, "alkynyl" refers to straight or branched chain hydrocarbyl groups having at least one carbon—carbon triple bond, and having in the range of about 2 up to 12 carbon atoms, and "substituted alkynyl" refers to alkynyl groups further bearing one or more substituents as set forth above.

As employed herein, "aryl" refers to aromatic groups having in the range of 6 up to 14 carbon atoms and "substituted aryl" refers to aryl groups further bearing one or more substituents as set forth above.

As employed herein, "heteroaryl" refers to aromatic groups having in the range of 4 up to about 13 carbon atoms, and at least one heteroatom selected from O, N, S, or the like; and "substituted heteroaryl" refers to heteroaryl groups further bearing one or more substituents as set forth above.

As employed herein, "alkylaryl" refers to alkyl-substituted aryl groups and "substituted alkylaryl" refers to alkylaryl groups further bearing one or more substituents as set forth above.

As employed herein, "arylalkyl" refers to aryl-substituted alkyl groups and "substituted arylalkyl" refers to arylalkyl groups further bearing one or more substituents as set forth above.

As employed herein, "arylalkenyl" refers to aryl-substituted alkenyl groups and "substituted arylalkenyl" refers to arylalkenyl groups further bearing one or more substituents as set forth above.

As employed herein, "alkenylaryl" refers to alkenyl-substituted aryl groups and "substituted alkenylaryl" refers to alkenylaryl groups further bearing one or more substituents as set forth above.

As employed herein, "arylalkynyl" refers to aryl-substituted alkynyl groups and "substituted arylalkynyl" refers to arylalkynyl groups further bearing one or more substituents as set forth above.

As employed herein, "alkynylaryl" refers to alkynyl-substituted aryl groups and "substituted alkynylaryl" refers to alkynylaryl groups further bearing one or more substituents as set forth above.

As employed herein, "arylene" refers to divalent aromatic groups typically having in the range of 6 up to 14 carbon atoms and "substituted arylene" refers to arylene groups further bearing one or more substituents as set forth above.

As employed herein, "aralkylene" refers to aryl-substituted divalent alkyl groups typically having in the range of about 7 up to 16 carbon atoms and "substituted aralkylene" refers to aralkylene groups further bearing one or more substituents as set forth above.

As employed herein, "aralkylene" refers to aryl-substituted divalent alkyl groups typically having in the range of about 7 up to 16 carbon atoms and "substituted aralkylene" refers to aralkylene groups further bearing one or more substituents as set forth above.

As employed herein, "aralkenylene" refers to aryl-substituted divalent alkenyl groups typically having in the range of about 8 up to 16 carbon atoms and "substituted aralkenylene" refers to aralkenylene groups further bearing one or more substituents as set forth above.

As employed herein, "aralkynylene" refers to aryl-substituted divalent alkynyl groups typically having in the range of about 8 up to 16 carbon atoms and "substituted aralkynylene" refers to aralkynylene group further bearing one or more substituents as set forth above.

As employed herein, "heterocyclic" refers to cyclic (i.e., ring-containing) groups containing one or more heteroatoms (e.g., N, O, S, or the like) as part of the ring structure, and having in the range of 3 up to 14 carbon atoms and "substituted heterocyclic" refers to heterocyclic groups further bearing one or more substituents as set forth above.

As employed herein, "heterocycloalkylene" refers to divalent cyclic (i.e., ring-containing) groups containing one or more heteroatoms (e.g., N, O, S, or the like) as part of the ring structure, and having in the range of 3 up to 14 carbon atoms and "substituted heterocycloalkylene" refers to heterocycloalkylene groups further bearing one or more substituents as set forth above.

As employed herein, "aroyl" refers to aryl-carbonyl species such as benzoyl and "substituted aroyl" refers to aroyl groups further bearing one or more substituents as set forth above.

As employed herein, "acyl" refers to alkyl-carbonyl species.

As employed herein, "halogen" refers to fluoride, chloride, bromide or iodide atoms.

As employed herein, reference to "a carbamate group" embraces substituents of the structure —O—C(O)—NR$_2$, wherein each R is independently H, alkyl, substituted alkyl, aryl or substituted aryl as set forth above.

As employed herein, reference to "a dithiocarbamate group" embraces substituents of the structure —S—C(S)—NR$_2$, wherein each R is independently H, alkyl, substituted alkyl, aryl or substituted aryl as set forth above.

As employed herein, reference to "a sulfonamide group" embraces substituents of the structure —S(O)$_2$—NH$_2$.

As employed herein, "sulfuryl" refers to substituents of the structure =S(O)$_2$.

As employed herein, "amino" refers to the substituent —NH$_2$.

As employed herein, "monoalkylamino" refers to a substituent of the structure —NHR, wherein R is alkyl or substituted alkyl as set forth above.

As employed herein, "dialkylamino" refers to a substituent of the structure —NR$_2$, wherein each R is independently alkyl or substituted alkyl as set forth above.

As employed herein, "alkoxycarbonyl" refers to —C(O)O—alkyl groups having in the range of 2 up to 20 carbon atoms and "substituted alkoxycarbonyl" refers to alkoxycarbonyl groups further bearing one or more substituents as set forth above.

As employed herein, reference to "an amide group" embraces substituents of the structure —C(O)—NR$_2$, wherein each R is independently H, alkyl, substituted alkyl, aryl or substituted aryl as set forth above. When each R is H, the substituent is also referred to as "carbamoyl", (i.e., a substituent having the structure —C(O)—NH$_2$). When only one of the R groups is H, the substituent is also referred to as "monoalkylcarbamoyl" (i.e., a substituent having the structure —C(O)—NHR, wherein R is alkyl or substituted alkyl as set forth above) or "arylcarbamoyl" (i.e., a substituent having the structure —C(O)—NH(aryl), wherein aryl is as defined above, including substituted aryl). When neither of the R groups are H, the substituent is also referred to as "di-alkylcarbamoyl" (i.e., a substituent having the structure —C(O)—NR$_2$, wherein each R is independently alkyl or substituted alkyl as set forth above).

As employed herein, "organosulfinyl" refers to substituents having the structure —S(O)-organo, wherein organo embraces alkyl-, alkoxy- and alkylamirio-moieties, as well as substituted alkyl-, alkoxy- or alkylamino-moieties.

As employed herein, "organosulfonyl" refers to substituents having the structure —S(O)2-organo, wherein organo embraces alkyl-, alkoxy- and alkylamino-moieties, as well as substituted alkyl-, alkoxy- or alkylamino-moieties.

In accordance with another embodiment of the present invention, there are provided synthetic methods for the preparation of invention compounds. For example, invention compounds can be prepared as illustrated in SCHEME 1.

SCHEME 1

Thus, an NSAID bearing a free carboxyl group (or a carboxy-substituted NSAID) can be contacted with an appropriately substituted hydroxamic acid in the presence or absence of a catalyst (e.g., dimethylaminopyridine (DMAP)), and a suitable coupling agent (e.g., 1,3-dicyclohexylcarbodiimide (DCC)) under conditions suitable to form invention compounds shown in SCHEME 1.

Similarly, thiohydroxamate derivatives of NSAIDs can be prepared as illustrated in SCHEME 2.

SCHEME 2

Thus an NSAID bearing a free carboxyl group (or a carboxy-substituted NSAID) can be contacted with an appropriately substituted thiohydroxamate in the presence or absence of a catalyst (e.g. DMAP) and a suitable coupling agent (e.g. DCC) under conditions suitable to for invention compounds as shown in SCHEME 2.

Employing similar synthetic strategies, a variety of heterocycle-containing derivatives of NSAIDs can be prepared, as illustrated, for example, in SCHEMEs 3 and 4.

SCHEME 3

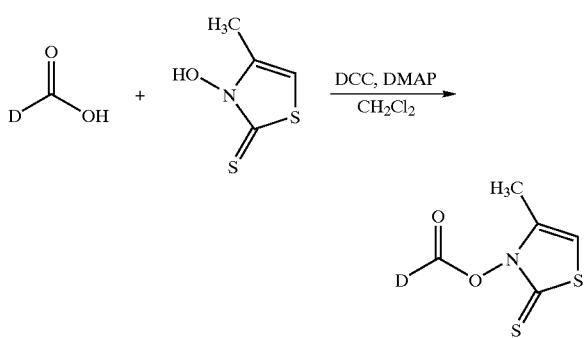

SCHEME 4

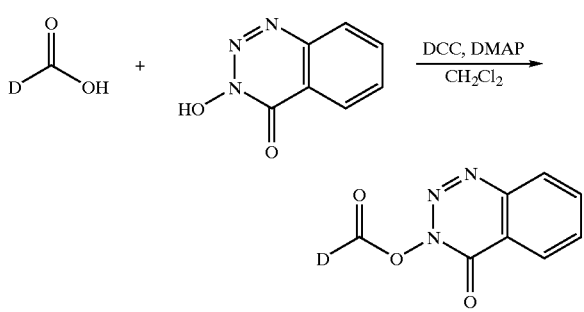

In accordance with yet another embodiment of the present invention, there are provided formulations containing invention compounds as described herein, in a pharmaceutically acceptable carrier. Exemplary pharmaceutically acceptable carriers include solids, solutions, emulsions, dispersions, micelles, liposomes, and the like. Optionally, the pharmaceutically acceptable carrier employed herein further comprises an enteric coating.

Pharmaceutically acceptable carriers contemplated for use in the practice of the present invention are those which render invention compounds amenable to oral delivery, transdernal delivery, intravenous delivery, intramuscular delivery, topical delivery, nasal delivery, and the like.

Thus, formulations of the present invention can be used in the form of a solid, a solution, an emulsion, a dispersion, a micelle, a liposome, and the like, wherein the resulting formulation contains one or more of the compounds of the present invention, as an active ingredient, in admixture with an organic or inorganic carrier or excipient suitable for enterable or parenteral applications. The active ingredient may be compounded, for example, with the usual non-toxic, pharmaceutically acceptable carriers for tablets, pellets, capsules, suppositories, solutions, emulsions, suspensions and any other suitable for use. The carriers which can be used include glucose, lactose, gum acacia, gelatin, manitol, starch paste, magnesium trisilicate, talc, corn starch, keratin, colloidal silica, potato starch, urea, medium chain length triglycerides, dextrans, and other carriers suitable for use in manufacturing preparations, in solid, semisolid, or liquid form. In addition auxiliary, stabilizing, thickening, and coloring agents and perfumes may be used. The active compound(s) is (are) included in the formulation in an amount sufficient to produce the desired effect upon the process or disease condition.

Invention formulations containing the active ingredient may be in a form suitable for oral use, for example, as tablets, troches, lozenges, aqueous or oily suspensions, dispersible powders or granules, emulsions, hard or soft capsules or syrups or elixirs. Formulations intended for oral use may be prepared according to any method known to the art for the manufacture of pharmaceutical compositions and such formulations may contain one or more agents selected from the group consisting of a sweetening agent such as sucrose, lactose, or saccharin, flavoring agents such as peppermint, oil of wintergreen or cherry, coloring agents and preserving agents in order to provide pharmaceutically elegant and palatable preparations. Tablets containing the active ingredient in admixture with non-toxic pharmaceutically acceptable excipients used may be, for example (1) inert diluents such as calcium carbonate, lactose, calcium phosphate or sodium phosphate; (2) granulating and disintegrating agents such corn starch, potato starch or alginic acid; (3) binding agents such as gum tragacanth, corn starch, gelatin or acacia, and (4) lubricating agents such as maganesium stearate, steric acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by such techniques as those described in U.S. Pat. Nos. 4,256,108; 4,160,452; and 4,265,874, to form osmotic therapeutic tablets for controlled release.

In some cases, formulations contemplated for oral use may be in the form of hard gelatin capsules wherein the active ingredient is mixed with inert solid diluent(s), for example, calcium carbonate, calcium phosphate or kaolin. They may also be in the form of soft gelatin capsules wherein the active ingredient is mixed with water or an oil medium, for example, peanut oil, liquid paraffin, or olive oil.

Invention formulations may be in the form of a sterile injectable suspension. This suspension may be formulated according to known methods using suitable dispersing or wetting agents and suspending agents. The sterile injectable preparation may also be a sterile injectable solution or suspension in a non-toxic parenterally-acceptable diluent or solvent, for example, as a solution in 1,3-butanediol. Sterile, fixed oils are conventionally employed as a solvent or suspending medium. For this purpose any bland fixed oil may be employed including synthetic mono- or diglycerides, fatty acids, naturally occurring vegetable oils like sesame oil, coconut oil, peanut oil, cottonseed oil, etc. , or synthetic fatty vehicles like ethyl oleate or the like. Buffers, preservatives, antioxidants, and the like can be incorporated as required.

Invention formulations may also be administered in the form of suppositories for rectal administration of the drug. These formulations may be prepared by mixing the drug with a suitable non-irritating excipient, such as cocoa butter, synthetic glyceride esters of polyethylene glycols, which are solid at ordinary temperatures, but liquefy and/or dissolve in the rectal cavity to release the drug. Since individual subjects may present a wide variation in severity of symptoms and each drug has its unique therapeutic characteristics, the precise mode of administration and dosage employed for each subject is left to the discretion of the practitioner.

Amounts effective for the particular therapeutic goal sought will, of course, depend on the severity of the condition being treated, and the weight and general state of the subject. Various general considerations taken into account in determining the "effective amount" are known to those of skill in the art and are described, e.g., in Gilman et al., eds., *Goodman And Gilman's: The Pharmacological Bases of Therapeutics*, 8th ed., Pergamon Press, 1990; and *Remington's Pharmaceutical Sciences*, 17th ed., Mack Publishing Co., Easton, Pa., 1990, each of which is herein incorporated by reference.

The term "effective amount" as applied to invention compounds, means the quantity necessary to effect the desired therapeutic result, for example, a level effective to treat, cure, or alleviate the symptoms of a disease state for which the therapeutic compound is being administered, or to establish homeostasis. Since individual subjects may present a wide variation in severity of symptoms and each drug or active agent has its unique therapeutic characteristics, the precise mode of administration, dosage employed and treatment protocol for each subject is left to the discretion of the practitioner.

In accordance with still another embodiment of the present invention, there are provided methods for treating inflammation and inflammation-related conditions. Such methods comprise administering to a subject in need thereof an effective amount of at least one invention compound as described herein.

Subjects contemplated for treatment in accordance with the present invention include mammals such as rodents, canines, felines, farm animals, primates, and the like, including humans.

Inflammation-related conditions contemplated for treatment in accordance with the present invention include arthritis (e.g rheumatoid arthritis, gouty arthritis, osteoarthritis, juvenile arthritis, systemic lupus erythematosus, spondyloarthopathies, and the like), gastrointestinal conditions (e.g., inflammatory bowel disease, Crohn's disease, gastritis, irritable bowel syndrome, ulcerative colitis, and the like), headache (e.g., migraine), asthma, bronchitis, menstrual cramps, tendinitis, bursitis, and the like.

As readily recognized by those of skill in the art, inflammation-related conditions are associated with a variety of conditions, such as, for example, vascular diseases, periarteritis nodosa, thyroidiris, aplastic anemia, Hodgkin's disease, sclerodoma, rheumatic fever, type I diabetes, myasthenia gravis, colorectal cancer, sarcoidosis, nephrotic syndrome, Behcet's syndrome, potymyositis, gingivitis, hypersensitivity, conjunctivitis, swelling occurring after injury, myocardial ischemia, and the like.

In accordance with a further embodiment of the present invention, there are provided methods for reducing side effects associated with anti-inflammatory agents. Such methods comprise employing, for example, an effective amount of an invention compound as described herein.

In accordance with yet another embodiment of the present invention, there are provided methods for promoting apoptosis in a subject. Such methods comprise administering to the subject an effective amount of an invention compound as described herein.

In accordance with a further embodiment of the present invention, there are provided methods of inhibiting the proliferation of a hyperproliferative mammalian cell in a subject in need thereof. Such methods comprise administering to the subject an effective amount of an invention compound as described herein.

In accordance with a still further embodiment of the present invention, there are provided methods for the treatment of cancer and/or tumor diseases through both promoting apoptosis and inhibiting MMP enzymes. Such methods comprise administrating to the subject an effective amount of an invention compound as described herein.

In accordance with a still further embodiment of the present invention, there are provided methods for enhancing antiinflammatory activity by the dual inhibition of cyclooxygenase and 5-lipoxygenase in a subject in need thereof. Such methods comprise administering to the subject an effective amount of an invention compound as described herein.

The invention will now be described in greater detail with reference to the following non-limiting examples.

EXAMPLES

The syntheses described in Examples 1–14 are illustrated in SCHEME 5.

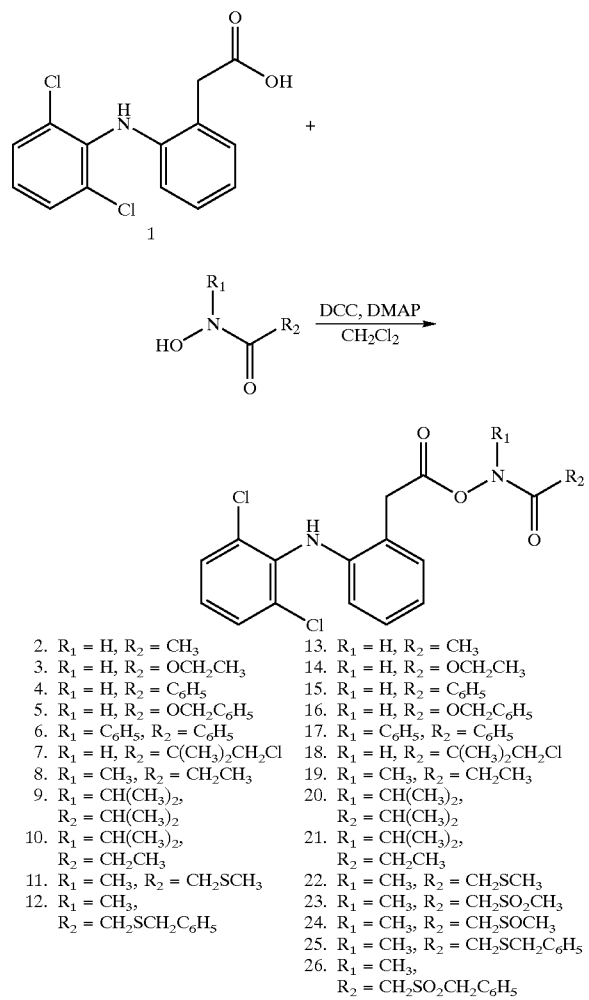

Scheme 5

2. $R_1 = H, R_2 = CH_3$
3. $R_1 = H, R_2 = OCH_2CH_3$
4. $R_1 = H, R_2 = C_6H_5$
5. $R_1 = H, R_2 = OCH_2C_6H_5$
6. $R_1 = C_6H_5, R_2 = C_6H_5$
7. $R_1 = H, R_2 = C(CH_3)_2CH_2Cl$
8. $R_1 = CH_3, R_2 = CH_2CH_3$
9. $R_1 = CH(CH_3)_2$, $R_2 = CH(CH_3)_2$
10. $R_1 = CH(CH_3)_2$, $R_2 = CH_2CH_3$
11. $R_1 = CH_3, R_2 = CH_2SCH_3$
12. $R_1 = CH_3$, $R_2 = CH_2SCH_2C_6H_5$

13. $R_1 = H, R_2 = CH_3$
14. $R_1 = H, R_2 = OCH_2CH_3$
15. $R_1 = H, R_2 = C_6H_5$
16. $R_1 = H, R_2 = OCH_2C_6H_5$
17. $R_1 = C_6H_5, R_2 = C_6H_5$
18. $R_1 = H, R_2 = C(CH_3)_2CH_2Cl$
19. $R_1 = CH_3, R_2 = CH_2CH_3$
20. $R_1 = CH(CH_3)_2$, $R_2 = CH(CH_3)_2$
21. $R_1 = CH(CH_3)_2$, $R_2 = CH_2CH_3$
22. $R_1 = CH_3, R_2 = CH_2SCH_3$
23. $R_1 = CH_3, R_2 = CH_2SO_2CH_3$
24. $R_1 = CH_3, R_2 = CH_2SOCH_3$
25. $R_1 = CH_3, R_2 = CH_2SCH_2C_6H_5$
26. $R_1 = CH_3$, $R_2 = CH_2SO_2CH_2C_6H_5$

Example 1

Compound 13 (Scheme 5). A solution of diclofenac (1) (2.96 g, 10 mmol), acetohydroxamic acid (2) (0.75 g, 10 mmol), 4-dimethylaminopyridine (DMAP) (0.12 g, 1 mmol) and 1,3-dicyclohexylcarbodiimide (DCC, 2.16 g, 10 mmol) was stirred at 0° C. for 3.5 h. The reaction mixture was filtered and the solvent was evaporated. The residue was partially dissolved in ethyl acetate and filtered. The ethyl acetate solution was washed with 0.5 N HCl solution, $Na_2CO_3$ solution and water. The organic solution was dried ($Na_2SO_4$) and the solvent was evaporated. The residue was purified by column chromatography on a silica gel column using $CH_2Cl_2$ and then 200:1 $CH_2Cl_2$/hexanes as eluents to give 0.39 g (11%) of compound 13 as a solid compound; $^1$H NMR($CDCl_3$) δ 2.04 (s, 3H), 3.99 (s, 2H, 1H ex $D_2O$), 6.55–6.57 (m, 2H), 6.97–7.00 (m, 2H), 7.13–7.16 (t, 1H), 7.26 (s, 1H), 7.32–7.34 (d, 2H), 9.35 (br, 1H, ex $D_2O$); MS (ESI) m/z 353 (M)$^+$.

Example 2

Compound 14 (Scheme 5). Compound 14 was synthesized from diclofenac (2.96 g, 10 mmol), compound 3 (1.05 g, 10 mmol), DMAP (0.12 g, 1 mmol) and DCC (2.06 g, 10 mmol) employing the procedure described in Example 1. The compound was purified by column chromatography on a silica gel column using $CH_2Cl_2$ as an eluent to give 1.17 g (31%) of compound 14 as a white solid. $^1$H NMR ($CDCl_3$) δ 1.24 (t, 3H), 3.97 (d, 2H), 4.22 (q, 2H), 6.55–6.58 (m, 2H, 1H, ex D2O), 6.98 (t, 2H), 7.15 (t, 1H), 7.27 (d, 1H), 7.33 (d, 2H), 8.13 (s, 1H, ex $D_2O$); MS (ESI) m/z 384 (M+H)$^+$.

Example 3

Compound 15 (Scheme 5). Compound 15 was synthesized from diclofenac (1) (1.48 g, 5 mmol), compound 4 (0.68 g, 5 mmol), DMAP (0.12 g, 1 mmol) and DCC (1.03 g, 5 mmol) employing the procedure described in Example 1. The compound was purified by crystallization from $CH_2Cl_2$/hexanes to give 1.3 g (65%) of compound 15 as a white solid. $^1$H NMR ($CDCl_3$) δ 4.08 (s, 2H), 6.58–6.59 (m, 2H, 1H, ex $D_2O$), 6.97–7.02 (m, 2H), 7.16 (t, 1H), 7.30–7.33 (m, 2H), 7.46 (t, 2H), 7.57 (t, 1H), 7.81 (d, 1H), 9.4 (br, 1H, ex $D_2o$); MS (ESI) m/z 437.7 (M+Na)$^+$.

Example 4

Compound 16 (Scheme 5). Compound 16 was synthesized from diclofenac (1) (1.48 g, 5 mmol), compound 5 (0.84 g, 5 mmol), DMAP (0.12 g, 1 mmol) and DCC (1.03 g, 5 mmol) employing the procedure described in Example 1. The compound was purified by crystallization from $CH_2Cl_2$/hexanes to give 0.93 g (42%) of compound 16 as a white solid. $^1$H NMR ($CDCl_3$) δ 3.97 (s, 2H), 5.19 (s, 2H), 6.53 (br, 1H, ex $D_2O$), 6.57 (d, 1H), 6.96–7.00 (m, 2H), 7.16 (t, 1H), 7.24 (d, 1H), 7.32–7.36 (m, 7H), 8.13 (s, 1H); MS (ESI) m/z 445.3 (M)$^+$.

Example 5

Compound 17 (Scheme 5). Compound 17 was synthesized from diclofenac (1) (1.48 g, 5 mmol), compound 6 (1.04 g, 5 mmol), DMAP (0.12 g, 1 mmol) and DCC (1.03 g, 5 mmol) employing the procedure described in Example 1. The compound was purified by column chromatography on a silica gel column using $CH_2Cl_2$ as an eluent to give 1.9 g (77%) of compound 17 as a white solid. $^1$H NMR ($CDCl_3$) δ 3.95 (s, 2H), 6.38 (br, 1H, ex $D_2O$), 6.54 (d, 1H), 6.94–6.99 (m, 2H), 7.13 (t, 1H), 7.18–7.32 (m, 11H), 7.52 (d, 2H); MS (ESI) m/z 491.5 (M)$^+$.

Example 6

Compound 18 (Scheme 5). Compound 18 was synthesized from diclofenac (1) (1.48 g, 5 mmol), compound 7 (0.58 g, 5 mmol), DMAP (0.12 g, 1 mmol) and DCC (1.03 g, 5 mmol) employing the procedure described in Example 1. The compound was purified by crystallization from $CH_2Cl_2$/hexanes to give 1.04 g (48%) of compound 18 as a white crystal. $^1$H NMR ($CDCl_3$) δ 1.36 (s, 6H), 3.63 (s, 2H), 4.01 (s, 2H), 6.51 (s, 1H, ex $D_2O$), 6.57 (d, 1H), 6.98 (t, 2H), 7.16 (t, 1H), 7.26–7.28 (m, 2H), 7.33 (d, 2H), 9.19 (s, 1H, ex $D_2O$); MS (ESI) m/z 429 (M)$^+$.

Example 7

Compound 8 (Scheme 5). To a solution of propionic acid (0.37 g, 0.37ml, 5 mmol) and DMF (0.2 ml) in $CH_2Cl_2$, was added slowly oxalyl chloride (1.32 g, 0.92 ml, 10.25 mmol) at room temperature. The resulting solution was stirred at room temperature for 30 min. In a separate flask, to a solution of methylhydroxyamine hydrochloride (1.67 g, 20 mmol) in a mixed solvent of THF (10 ml) and $H_2O$ (1.5 ml) was added triethylamine (TEA) (4.2 ml, 30 mmol) at 0° C. and stirred for 20 min. The propionic acid-oxalyl chloride solution prepared above was slowly dripped into the methylhydroxylamine solution. Stirring of the resulting solution was continued at room temperature for 1 hour. A solution of 2N HCl (100 ml) was added to the reaction mixture. The solution was extracted three times with $CH_2Cl_2$. The $CH_2Cl_2$ solution was dried with sodium sulfate ($Na_2SO_4$) and the solvent was evaporated to give 80 mg (16%) of compound 7 as an oil. $^1$H NMR ($CDCl_3$) δ 1.19 (t, 3H), 1.62 (br, 1H, ex $D_2O$), 2.35 (q, 2H), 3.33 (s, 3H); MS (ESI) m/z 103 (M)$^+$.

Compound 19 (Scheme 5). Compound 19 was synthesized from diclofenac (1) (0.23 g, 0.8 mmol), compound 8 (0.08 g, 0.8 mmol), DCC (0.16 g, 0.8 mmol) and DMAP (0.06 g, 0.5 mmol) employing the procedure described in Example 1. The compound was purified by column chromatography on a silica gel column using $CH_2Cl_2$ as an eluent to give 150 mg (30%) of compound 19 as a solid. $^1$H NMR ($CDCl_3$) δ 1.03 (t, 3H), 2.19 (q, 2H), 3.29 (s, 3H), 3.94 (s, 2H), 6.54 (br, 1H, ex $D_2O$), 6.58 (d, 1H), 6.99–7.02 (m, 2H), 7.17 (t, 1H), 7.27 (s, 1H), 7.35 (d, 2H) (ESI) m/z 381.4 (M)$^+$.

Example 8

Compound 9 (Scheme 5). A mixture of isopropylhydroxylamine hydrochloride and $K_2CO_3$ in acetonitrile was stirred at room temperature for 2 h. A solution of isobutyl chloride in a 20 ml of $CH_3CN$ was dropped into the above mixture at 0° C. and then stirred at room temperature for 4 days. Water was added and the mixture was extracted four times with $CH_2Cl_2$. The organic phase was washed with brine and dried ($Na_2SO_4$) and the solvent was evaporated to give 0.36 g (50%) of compound 9 as a pale yellow solid. $^1$H NMR ($CDCl_3$) δ 1.17 (d, 6H), 1.32 (d, 6H), 2,72 (m, 1H), 4.25 (m, 1H), 8.3 (br, 1H, ex $D_2O$); MS (ESI) m/z 144.4 (M−1)$^+$.

Compound 20 (Scheme 5). Compound 20 was synthesized from diclofenac (1) (0.23 g, 0.8 mmol), compound 9 (0.12 g, 0.8 mmol), DCC (0.16 g, 0.8 mmol) and DMAP (0.06 g, 0.5 mmol) employing the procedure described in Example 1. The compound was purified by column chromatography on a silica gel column using $CH_2Cl_2$ as an eluent to give 0.3 g (88%) of compound 20 as a solid. $^1$H NMR ($CDCl_3$) δ 1.02 (d, 6H), 1.11 (d, 6H), 2.42 (m, 1H), 3.98 (s, 2H), 4.7 (m, 1H), 6.55 (br, 1H, ex $D_2O$), 6.58 (d, 1H), 6.97–7.39 (m, 6H); MS (ESI) m/z 423.5 (M)$^+$.

Example 9

Compound 10 (Scheme 5). Compound 10 was synthesized from propionic acid (0.74 g, 0.74 ml, 10 mmol), isopropylhydroxyamine hydrochloride (2.22 g, 20 mmol) and oxalyl chloride (0.92 ml, 1.32 g, 10.25 mmol) employing the procedure described in the first paragraph of Example 7. The reaction generated 0.3 g (23%) of compound 10 as an oil. $^1$H NMR ($CDCl_3$) δ 1.20 (m, 3H), 1.31

(m, 6H), 2.37 (q, 2H), 4.17 (m, 1H), 8.21 (br, 1H, ex D$_2$O); MS (ESI) m/z 132.2 (M+1)$^+$.

Compound 21 (Scheme 5). Compound 21 was synthesized from diclofenac (0.67 g, 2.2 mmol), compound 10 (0.3 g, 2.2 mmol), DCC (0.47 g, 2.3 mmol) and DMAP (0.04 g, 0.3 mmol) employing the procedure described in Example 1. The compound was purified by column chromatography on a silica gel column using CH$_2$Cl$_2$ as an eluent to give 0.7 g (78%) of compound 21 as a pale yellow solid. $^1$H NMR (CDCl$_3$) δ 1.03 (t, 3H), 1.09 (d, 6H), 2.15 (q, 1H), 3.98 (s, 2H), 4.76 (br, 1H), 6.57 (br, 1H, ex D$_2$O), 6.57 (d, 1H), 6.98–7.36 (m, 6H); MS (ESI) m/z 431.9 (M+H)$^+$.

Example 10

Compound 11 (Scheme 5). Compound 11 was synthesized from (methylthio)acetic acid (1.06 g, 10 mmol), methylhydroxylamine hydrochloride (3.34 g, 40 mmol), and oxalyl chloride (1.84 ml, 20.5 mmol) employing the procedure described in the first paragraph of Example 7. The reaction generated 0.85 g (63%) of compound 11 as an oil. The compound was used to synthesize compound 22 without further purification.

Compound 22 (Scheme 5). Compound 22 was synthesized from diclofenac (1.84 g, 6.2 mmol), compound 11 (0.85 g, 6.2 mmol), DCC (1.36 g, 6.6 mmol) and DMAP (0.12 g, 1 mmol) employing the procedure described in Example 1. The compound was purified by column chromatography on a silica gel column using CH$_2$Cl$_2$ and CH$_2$Cl$_2$/CH$_3$OH (100/1) as eluents to give 0.91 g (36%) of compound 22 as a solid compound. $^1$H NMR (CDCl$_3$) δ 2.11 (s, 3H), 3.12(s, 2H), 3.35 (s, 3H), 3.96 (s, 2H), 6.47 (br, 1H, ex D$_2$O), 6.58 (d, 1H), 6.98–7.35 (m, 6H); MS (ESI) m/z 413.5 (M)$^+$.

Example 11

Compound 23 (Scheme 5). To a solution of compound 22 (0.98 g, 2.4 mmol) in 30 ml of acetone was added 3-chloroperoxybenzoic acid (m-CPBA) (1.03 g, 6 mmol) at 0° C. The resulting solution was stirred at 0° C. for 2 h. A solution of sodium bisulfite was added and stirred at 0° C. for 5 min. Water was added to the above solution and stirred for 2 hrs. The suspension was filtered and the solid was dissolved in CH$_2$Cl$_2$ and purified by column chromatography on a silica gel column using CH$_2$Cl$_2$ and CH$_2$Cl$_2$/MeOH (50/1) as eluents to give 0.59 g (55%) of compound 23 as a solid. $^1$H NMR (CDCl$_3$) δ 3.08 (s, 3H), 3.38 (s, 3H), 3.92 (s, 2H), 3.99 (s, 2H), 6.34 (br, 1H, ex D$_2$O), 6.57 (d, 1H), 6.99–7.04 (q, 2H), 7.18 (t, 1H), 7.28 (d, 1H), 7.35 (d, 2H); MS (ESI) m/z 447.9 (M+H)$^+$.

Example 12

Compound 24 (Scheme 5). To a solution of compound 22 (0.49 g, 1.2 mmol) in 30 ml of acetone was added 3-chloroperoxybenzoic acid (m-CPBA) (0.25 g, 1.42 mmol) at 0° C. The resulting solution was stirred at 0° C. for 2 h. A solution of sodium bisulfite was added and stirred at 0° C. for 5 min. Water was added to the above solution and stirred for 10 min. The mixture was extracted three times with CH$_2$Cl$_2$. The combined organic solution was washed with brine and dried (Na$_2$SO$_4$). The solvent was evaporated and the residue was purified by column chromatography on a silica gel column using CH$_2$Cl$_2$ and CH$_2$Cl$_2$/MeOH (50/1) as eluents to give 0.42 g (84%) of compound 24 as an oil. $^1$H NMR (CDCl$_3$) δ 264 (s, 3H), 3.34 (s, 3H), 3.55 (m, 1H), 3.58 (m, 1H), 3.98 (s, 2H), 6.44 (br, 1H, ex D$_2$O), 6.57 (d, 1H), 7.01. (m, 2H), 7.18 (t, 1H), 7.28 (d, 1H), 7.33 (d, 2H); MS (ESI) m/z 451.5 (M+Na)$^+$.

Example 13

Compound 12 (Scheme 5). Compound 12 was synthesized from benzylthioglycolic acid (1.82 g, 10 mmol), methylhydroxylamine hydrochloride (3.34 g, 40 mmol), oxalyl chloride (1.84 ml, 2.64 g, 20.5 mmol), TEA (8.4 ml, 6.06 g, 60 mmol) and DMF (0.4 ml, 10 mmol) employing the procedure described in the first paragraph of Example 7. The reaction generated 2.1 g (99%) of compound 12 as a pale yellow oil; The compound was used to make compound 25 without further characterization.

Compound 25 (Scheme 5). Compound 25 was synthesized from diclofenac (1) (2.96 g, 10 mmol), compound 12 (2.1 g, 10 mmol), DCC (2.06 g, 10 mmol) and DMAP (0.02 g, 0.2 mmol) employing the procedure described in Example 1. The compound was purified by column chromatography on a silica gel column using CH$_2$Cl$_2$ as an eluent to give 3.6 g (74%) of compound 25 as an oil; $^1$H NMR (CDCl$_3$) δ 3.05 (s, 2H), 3.34 (s, 3H), 3.74 (s, 2H), 3.91 (s, 2H), 6.48 (br, 1H, ex D$_2$O), 6.57–7.50 (m, 12H); MS (ESI) m/z 489.5 (M)$^+$.

Example 14

Compound 26 (Scheme 5). Compound 26 was synthesized from compound 25 (0.97 g, 2 mmol) and m-CPBA (0.51 g, 2.1 mmol) employing the procedure set forth in Example 11. The compound was purified by crystallization from CH$_2$Cl$_2$/hexanes to give 0.62 g (60%) of compound 26 as a white crystal; $^1$H NMR (CDCl$_3$) δ 3.39 (s, 3H), 3.71 (s, 2H), 3.95 (s, 2H), 4.48 (s, 2H), 6.31 (br, 1H, ex D$_2$O), 6.56–7.59 (m, 12H); MS (ESI) m/z 522.4 (M+H)$^+$.

The syntheses described in Examples 15–28 are illustrated in SCHEME 6.

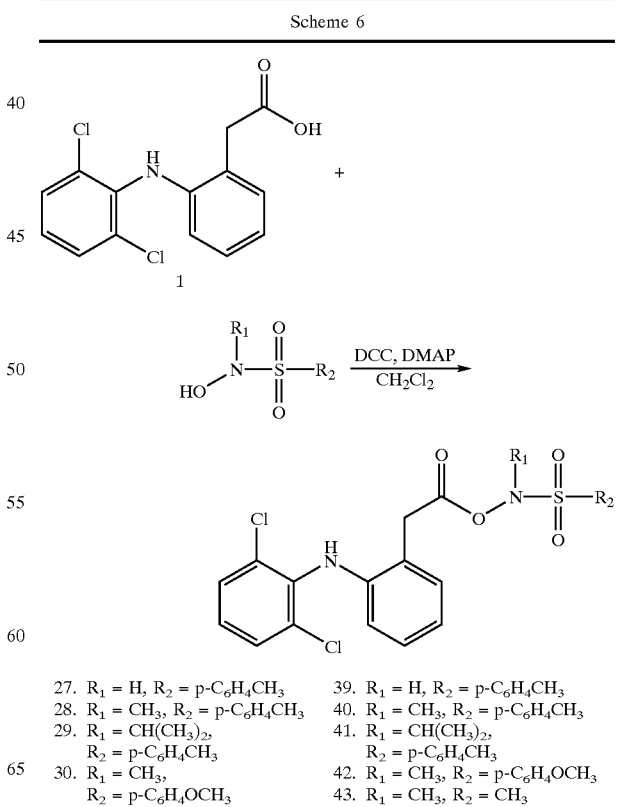

Scheme 6

27. R$_1$ = H, R$_2$ = p-C$_6$H$_4$CH$_3$
28. R$_1$ = CH$_3$, R$_2$ = p-C$_6$H$_4$CH$_3$
29. R$_1$ = CH(CH$_3$)$_2$, R$_2$ = p-C$_6$H$_4$CH$_3$
30. R$_1$ = CH$_3$, R$_2$ = p-C$_6$H$_4$OCH$_3$

39. R$_1$ = H, R$_2$ = p-C$_6$H$_4$CH$_3$
40. R$_1$ = CH$_3$, R$_2$ = p-C$_6$H$_4$CH$_3$
41. R$_1$ = CH(CH$_3$)$_2$, R$_2$ = p-C$_6$H$_4$CH$_3$
42. R$_1$ = CH$_3$, R$_2$ = p-C$_6$H$_4$OCH$_3$
43. R$_1$ = CH$_3$, R$_2$ = CH$_3$

-continued

Scheme 6

| | |
|---|---|
| 31. $R_1 = CH_3$, $R_2 = CH_3$ | 44. $R_1 = CH_3$, $R_2 = p\text{-}C_6H_4NO_2$ |
| 32. $R_1 = CH_3$, $R_2 = p\text{-}C_6H_4NO_2$ | 45. $R_1 = CH_3$, $R_2 = CH_2CH_3$ |
| 33. $R_1 = CH_3$, $R_2 = CH_2CH_3$ | 46. $R_1 = CH_3$, $R_2 = m\text{-}C_6H_4CF_3$ |
| 34. $R_1 = CH_3$, $R_2 = m\text{-}C_6H_4CF_3$ | 47. $R_1 = CH_3$, $R_2 = CH_2CH_2CH_2CH_3$ |
| 35. $R_1 = CH_3$, $R_2 = CH_2CH_2CH_2CH_3$ | 48. $R_1 = CH_3$, $R_2 = 2,4,6\text{-}C_6H_2(CH_3)_3$ |
| 36. $R_1 = CH_3$, $R_2 = 2,4,6\text{-}C_6H_2(CH_3)_3$ | 49. $R_1 = CH_3$, $R_2 = CH_2CH_2CH_3$ |
| 37. $R_1 = CH_3$, $R_2 = CH_2CH_2CH_3$ | 50. $R_1 = H$, $R_2 = 2,4,6\text{-}C_6H_2(CH_3)_3$ |
| 38. $R_1 = H$, $R_2 = 2,4,6\text{-}C_6H_2(CH_3)_3$ | 51. $R_1 = CH_2CH_2CH_2SO_3Na$, $R_2 = p\text{-}C_6H_4CH_3$ |
| | 52. $R_1 = CH_2CH_2CH_2CH_2SO_3Na$, $R_2 = p\text{-}C_6H_4CH_3$ |

Example 15

Compound 27 (Scheme 6). A solution of hydroxylamine hydrochloride (1.38 g, 20 mmol) and TEA (4.2 ml, 3.03 g, 30 mmol) in a mixed solvent of 40 ml of THF and 6 ml of $H_2O$ was stirred at 0° C. for 15 min. A solution of p-toluenesulfonyl chloride (0.95 g, 5 mmol) in 10 ml of THF was dripped into the above solution at 0° C. The resulting solution was stirred at 0° C. for 2.5 h. Water (400 ml) was added and the solution was extracted with ethyl acetate twice. The combined organic solution was washed with $H_2O$ three times and dried ($Na_2SO_4$). The solvent was evaporated and the residue was dissolved in $CH_2Cl_2$ and cooled down to −10° C. to give white crystalline solid. The compound was dried to give 0.28 g (30%) of compound 27 as a white solid. $^1$H NMR ($CDCl_3$) δ 2.46 (s, 3H), 6.07 (d, 1H, ex $D_2O$), 6.65 (d, 1H, ex $D_2O$), 7.36 (d, 2H), 7.84 (d, 2H); MS (ESI) m/z 186.3 (M-H)$^-$.

Compound 39 (Scheme 6). Compound 39 was synthesized from diclofenac (1) (0.44 g, 1.5 mmol), compound 27 (0.28 g, 1.5 mmol), DCC (0.31 g, 1.5 mmol) and DMAP (0.012 g, 0.1 mmol) employing the procedure described in Example 1. The compound was purified by column chromatography on a silica gel column using $CH_2Cl_2$ as an eluent to give 0.23 g (33%) of compound 39 as an pale yellow solid. $^1$H NMR ($CDCl_3$) δ 2.21(s, 3H), 3.77 (s, 2H), 6.17 (s, 1H, ex $D_2O$), 6.49 (d, 1H), 6.06–7.01 (q, 2H), 7.10–7.18(m, 4H), 7.32 (d, 2H), 7.68 (d, 2H), 8.98 (s, 1H, ex $D_2O$);MS (ESI) m/z 451.5 (M+Na)$^+$.

Example 16

Compound 28 (Scheme 6). Compound 28 was synthesized from p-toluenesulfonyl chloride (0.95 g, 5mmol) and methylhydroxylamine hydrochloride (0.83 g, 10 mmol) employing the procedure described in the first paragraph of Example 15. The compound was purified by column chromatography on a silica gel column using $CH_2Cl_2$ to give 0.69 g (68%) of compound 28 as a white solid. $^1$H NMR ($CDCl_3$) δ 2.47 (s, 3H), 2.82 (s, 3H), 6.35 (s, 1H, ex $D_2O$), 7.37 (d, 2H), 7.78 (d, 2H).

Compound 40 (Scheme 6). Compound 40 was synthesized from diclofenac (1) (0.3 g, 1 mmol) and compound 28 (0.2 g, 1 mmol) employing the procedure described in Example 1. The compound was purified by column chromatography on a silica gel column using $CH_2Cl_2$ as an eluent to give 0.42 g (87%) of compound 40 as a white foam; $^1$H NMR ($CDCl_3$) δ 2.37 (s, 3H), 3.02 (s, 3H), 3.83 (s, 2H), 6.31 (br, 1H, ex $D_2O$), 6.56 (d, 1H), 6.96–7.00 (m, 2H), 7.15–7.19 (m, 2H), 7.24 (s, 2H), 7.32 (d, 2H), 7.65 (d, 2H); MS (ESI) m/z 502.2 (M+Na)$^+$.

Example 17

Compound 29 (Scheme 6). Compound 29 was synthesized from p-toluenesulfonyl chloride (0.95 g, 5 mmol) and isopropylhydroxylamine hydrochloride (1.2 g, 10 mmol) employing the procedure described in the first paragraph of Example 15. The compound was purified by column chromatography on a silica gel column using $CH_2Cl_2$ as an eluent to give 0.33 g (29%) of compound 29 as a white solid.

Compound 41 (Scheme 6). Compound 41 was synthesized from diclofenac (1) (0.42 g, 1.43 mmol), compound 29 (0.33 g, 1.43 mmol), DCC (0.3 g, 1.43 mmol) and DMAP (0.02 g, 0.2 mmol) employing the procedure described in Example 1. The compound was purified by column chromatography on a silica gel column using $CH_2Cl_2$ as an eluent to give 0.39 g (54%) of compound 41 as pale yellow solid. $^1$H NMR ($CDCl_3$) δ 1.16 (d, 6H), 2.25 (s, 3H), 3.78 (s, 2H), 4.3 (m, 1H), 6.31 (br, 1H, ex $D_2O$), 6.52 (d, 1H), 6.96–7.00 (m, 2H), 7.11–7.20 (m, 4H), 7.32 (d, 2H), 7.68 (d, 2H); MS (ESI) m/z 530.0 (M+Na)$^+$.

Example 18

Compound 30 (Scheme 6). Compound 30 was synthesized from 4-methoxybenzenesulfonyl chloride (1.03 g, 5 mmol) and methylhydroxylamine hydrochloride (0.83 g, 10 mmol) ) employing the procedure described in the first paragraph of Example 15. The compound was purified by simple extraction to give 0.63 g (58%) of compound 30 as a white solid. $^1$H NMR ($CDCl_3$) δ 2.81 (s, 3H), 3.89 (s, 3H), 3.75 (s, 1H, ex $D_2O$), 7.04 (q, 2H), 7.82 (q, 2H).

Compound 42 (Scheme 6). Compound 42 was synthesized from diclofenac (0.89 g, 3 mmol) and compound 30 (0.65 g, 3 mmol) employing the procedure described in Example 1. The compound was purified by chromatography on a silica gel column using $CH_2Cl_2$ as an eluent to give 0.9 g (61%) of compound 42 as a white solid. $^1$H NMR ($CDCl_3$) δ 3.02 (s, 3H), 3.81 (s, 3H), 3.84 (s, 2H), 6.31 (br, 1H ex $D_2O$), 6.56 (d, 1H), 6.89 (d, 2H), 6.98 (q, 2H), 7.16 (q, 2H), 7.32 (d, 2H), 7.69 (d, 2H); MS (ESI) m/z 530.0 (M+Na)$^+$.

Example 19

Compound 31 (Scheme 6). Compound 31 was synthesized from methanesulfonyl chloride (0.81 ml, 1.2 g, 10 mmol) and methylhydroxylamine hydrochloride (1.66 g, 20 mmol) employing the procedure described in the first paragraph of Example 15. The reaction generated 0.63 g (50%) of compound 31 as a white solid. $^1$H NMR ($CDCl_3$) δ 2.94 (s, 3H), 3.05 (s, 3H), 6.91 (s, 1H, ex $D_2O$); MS (ESI) m/z 148.2 (M+Na)$^+$.

Compound 43 (Scheme 6). Compound 43 was synthesized from diclofenac (1.48 g, 5 mmol) and compound 31 (0.63 g, 5 mmol) employing the procedure described in Example 1. The compound was purified by crystallization using $CH_2Cl_2$/hexanes to give 1.47 g (73%) of compound 43 as a white solid. $^1$H NMR ($CDCl_3$) δ 2.91 (s, 3H), 3.17 (s, 3H), 3.94 (s, 2H), 6.47 (br, 1H, ex $D_2O$), 6.59 (d, 1H), 6.98 (q, 2H), 7.16 (t, 1H), 7.26 (s, 1H), 7.34 (d, 2H); MS (ESI) m/z 403.5 (M)$^+$.

Example 20

Compound 32 (Scheme 6). Compound 32 was synthesized from 4-nitrobenzenesulfonyl chloride (1.11 g, 5 mmol) and methylhydroxylamine hydrochloride (0.83 g, 10 mmol) employing the procedure described in the first paragraph of Example 15. Purification by extraction gave 0.6 g (52%) of compound 32 as an yellow solid.

Compound 44 (Scheme 6). Compound 44 was synthesized from diclofenac (0.76 g, 2.6 mmol), compound 32 (0.6 g, 2.6 mmol), DCC (0.62 g, 3 mmol) and DMAP (0.02 g, 0.2 mmol) employing the procedure described in Example 1. The compound was purified by column chromatography on a silica gel column using $CH_2Cl_2$ as an eluent to give 0.97 g (73%) of compound 44 as a pale yellow solid. $^1$H NMR ($CDCl_3$) δ 3.11 (s, 3H), 3.83 (s, 2H), 6.15 (br, 1H, ex $D_2O$), 6.54 (d, 1H), 6.98–7.04 (m, 2H), 7.16–7.26 (m, 2H), 7.32 (d, 2H), 7.84 (q, 2H), 8.19 (q 2H); MS (ESI) m/z 511 (M+H)$^+$.

Example 21

Compound 33 (Scheme 6). Compound 33 was synthesized from ethanesulfonyl chloride (1.28 g, 10 mmol) and methylhydroxylamine hydrochloride (0.83 g, 10 mmol) employing the procedure described in the first paragraph of Example 15. The compound was purified by simple extraction to give 0.97 g (70%) of compound 33 as a white oil. $^1$H NMR ($CDCl_3$) δ 1.46 (t, 3H), 3.08 (s, 3H), 3.18 (q, 2H), 6.49 (s, 1H, ex $D_2O$).

Compound 45 (Scheme 6). Compound 45 was synthesized from diclofenac (1.95 g, 6.6 mmol), compound 33 (0.92 g, 6.6 mmol), DCC (1.36 g, 6.6 mmol) and DMAP (0.12 g, 1 mmol) employing the procedure described in Example 1. The compound was purified by crystallization from $CH_2Cl_2$/hexanes to give 2.1 g (76%) of compound 45 as a white solid. $^1$H NMR ($CDCl_3$) δ 1.36 (t, 3H), 3.02 (q, 2H), 3.17 (s, 3H), 3.92 (s, 2H), 6.5 (br, 1H ex $D_2O$), 6.58 (d, 1H), 7.00 (t, 2H), 7.16 (t, 1H), 7.26 (q, 1H), 7.34 (d, 2H); MS (ESI) m/z 417.4 (M)$^+$.

Example 22

Compound 34 (Scheme 6). Compound 34 was synthesized from 3-(trifluoromethyl)benzenesulfonyl chloride (1.22 g, 5 mmol), methylhydroxyamine hydrochloride (0.83 g, 10 mmol) employing the procedure described in the first paragraph of Example 15. The compound was purified simply by extraction to give 0.65 g (51%) of compound 34 as a solid.

Compound 46 (Scheme 6). Compound 46 was synthesized from diclofenac (0.74 g, 2.5 mmol), compound 34 (0.65 g, 2.5 mmol), DCC (0.51 g, 2.5 mmol) and DMAP (0.02 g, 0.2 mmol) employing the procedure described in Example 1. The compound was purified by column chromatography on a silica gel column using $CH_2Cl_2$ as an eluent to give 0.46 g (35%) of compound 46 as a white solid; $^1$H NMR ($CDCl_3$) δ 3.05 (s, 3H), 3.85 (s, 2H), 6.27 (br, 1H, ex $D_2O$), 6.57 (d, 1H), 6.97–7.01 (q, 2H), 7.17–7.18 (m, 2H), 7.32 (d, 2H), 7.60 (t, 1H), 7.88 (d, 2H), 8.14 (s, 1H); MS (ESI) m/z 533.7 (M)$^+$.

Example 23

Compound 35 (Scheme 6). Compound 35 was synthesized from butylsulfonyl chloride (1.56 g, 10 mmol) and methylhydroxylamine hydrochloride (0.83 g, 10(mmol) employing the procedure described in the first paragraph of Example 15. The compound was purified by simple extraction to give 1.46 g (87%) of compound 35 as a white solid. $^1$H NMR ($CDCl_3$) δ 0.97 (t, 3H), 1.50 (m, 2H), 1.88 (m, 2H), 3.06 (s, 2H), 3.13 (t, 2H), 6.80 (br, 1H, ex $D_2O$).

Compound 47 (Scheme 6). Compound 47 was synthesized from diclofenac (2.58 g, 8.7 mmol), compound 35 (1.46 g, 8.7 mmol), DCC (1.79 g, 8.7 mmol) and DMAP (0.12 g, 1 mmol) employing the procedure described in Example 1. The compound was purified by column chromatography on a silica gel column using $CH_2Cl_2$/Hexanes as an eluent to give 2.1 g (54%) of compound 47 as a pale yellow solid. $^1$H NMR ($CDCl_3$) δ 0.85 (t, 3H), 1.32 (m, 2H), 1.77 (m, 2H), 2.95 (t, 2H), 3.16 (s, 3H), 3.92 (s, 2H), 6.54 (br, 1H, ex $D_2O$), 6.58 (d, 1H), 7.00 (m, 2H), 7.16 (t, 1H), 7.26 (d, 1H), 7.36 (d, 2H); MS (ESI) m/z 478.4 (M+Na)$^+$.

Example 24

Compound 36 (Scheme 6). Compound 36 was synthesized from 2-mesitylenesulfonyl chloride (2.18 g, 10 mmol) and methylhydroxylamine hydrochloride (0.83 g, 10 mmol) employing the procedure described in the first paragraph of Example 15. The compound was purified by simple extraction to give 1.5 g (66%) of compound 36 as a white solid. $^1$H NMR ($CDCl_3$) δ 2.31 (s, 3H), 2.66 (s, 6H), 3.02 (s, 3H), 6.98(s, 1H); MS (ESI) m/z 252.5 (M+Na)$^+$.

Compound 48 (Scheme 6). Compound 48 was synthesized from diclofenac (1) (1.93 g, 6.5 mmol), compound 36 (1.5 g, 6.5 mmol), DCC (1.33 g, 6.5 mmol) and DMAP (0.12 g, 1 mmol) employing the procedure described in Example 1. The, compound was purified by column chromatography on a silica gel column using $CH_2Cl_2$ as an eluent to give 2.84 g (86%) of compound 48 as an pale yellow solid. $^1$H NMR ($CDCl_3$) δ 1.96 (s, 3H), 2.67 (s, 6H), 3.21 (s, 3H), 3.51 (s, 2H), 6.21 (br, 1H, ex $D_2O$), 6.44 (d, 1H), 6.77 (s, 2H), 6.90 (t, 1H), 6.98 (t, 1H), 7.09 (t, 1H), 7.33 (d, 2H); MS (ESI) m/z 507.0 (M)$^+$.

Example 25

Compound 37 (Scheme 6). Compound 37 was synthesized from propanesulfonyl chloride (1.42 g, 10 mmol) and methylhydroxylamine hydrochloride (0.83 g, 10 mmol) employing the procedure described in the first paragraph of Example 15. The compound was purified by simple extraction to give 1.35 g (88%) of compound 37 as a white oil. $^1$H NMR ($CDCl_3$) δ 1.09 (t, 3H), 1.94 (m, 2H), 3.09 (s 3H), 3.11 (t, 2H); MS (ESI) m/z 176.2 (M+Na)$^+$.

Compound 49 (Scheme 6). Compound 49 was synthesized from diclofenac (1) (2.53 g, 8.55 mmol), compound 37 (1.31 g, 8.55 mmol), DCC (1.79 g, 8.7 mmol) and DMAP (0.12 g, 1 mmol) employing the procedure described in Example 1. The compound was purified by column chromatography on a silica gel column using $CH_2Cl_2$ as an eluent to give 2.0 g (88%) of compound 49 as a pale yellow solid. $^1$H NMR ($CDCl_3$) δ 0.95 (t, 3H), 1.83 (m, 2H), 2.92 (t, 2H), 3.16 (s, 3H), 3.92 (s, 2H), 6.53 (br, 1H, ex $D_2O$), 6.57 (d, 1H), 7.01 (t, 2H), 7.16 (t, 1H), 7.26 (d, 1H), 7.35 (d, 2H); MS (ESI) m/z 431.8 (M+H)$^+$.

Example 26

Compound 38 (Scheme 6). Compound 38 was prepared from 2-mesitylenesulfonyl chloride (2.18 g, 10 mmol), hydroxyamine hydrochloride (1.38 g, mmol) employing the procedure described in the first paragraph of Example 15. The compound was purified by column chromatography on a silica gel column to give 1.07 g (50%) of the compound 38 as a white solid. $^1$H NMR ($CDCl_3$) δ 2.26 (s, 3H), 3.32 (s, 6H), 9.24 (d, 1H, ex $D_2O$), 9.41 (d, 1H, ex $D_2O$).

Compound 50 (Scheme 6). Compound 50 was prepared from diclofenac (1) (0.55 g, 1.85 mmol), compound 38 (0.4 g, 1.85 mmol), DCC (0.38 g, 1.85 mmol) and DMAP (0.12 g, 1 mmol) employing the procedure described in Example 1. The compound was purified by column chromatography on a silica gel column using $CH_2Cl_2$ as an eluent to give 0.5 g (55%) of compound 50 as a pale yellow solid. $^1$H NMR (CDCl$_3$) δ 2.09 (s, 3H), 2.63 (s, 6H), 2.75 (s, 2H), 6.21 (br, 1H, ex D$_2$O), 6.48 (d, 1H), 6.84 (s, 2H), 6.95 (t, 1H), 6.99 (t, 1H), 7.13 (t, 1H), 7.33 (d, 2H); MS (ESI) m/z 494.5 (M+H)$^+$.

Example 27

Compound 51 (Scheme 6). To a stirring solution of compound 39 in dimethylformamide at room temperature under N$_2$ is added sodium hydride. The resulting mixture was stirred at room temperature for 1 h. Propane sultone was added to the above solution and stirred at room temperature overnight to give the desired compound 51 after purification.

Example 28

Compound 52 (Scheme 6). Compound 52 is prepared from compound 39 and 1,4-butane sultone employing the procedure described in Example 27. The compound is purified by column chromatography on a silica gel column.

Example 29

The synthesis described in Example 29 is illustrated in SCHEME 7.

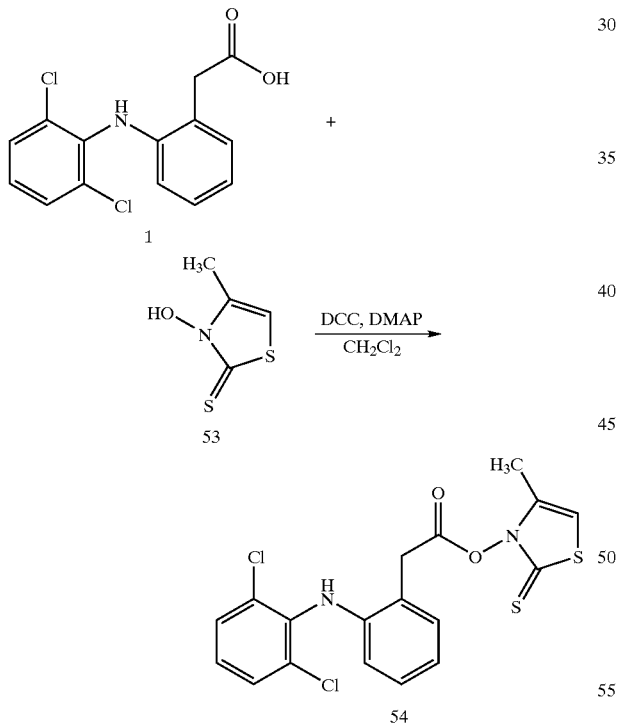

Compound 54 (Scheme 7). Compound 54 was synthesized from diclofenac (1) (1.48 g, 5 mmol), compound 53 (0.73 g, 5 mmol), DCC (1.03 g, 5 mmol) and DMAP (0.12 g, 1 mmol) employing the procedure described in Example 1. The compound was purified by crystallization from CH$_2$Cl$_2$/hexanes to give 0.77 g (36%) of compound 54 as a white solid. $^1$H NMR (CDCl$_3$) δ 2.06 (d, 3H), 4.24 (d, 2H), 6.21 (s, 1H), 6.98–7.03 (m, 2H), 7.19 (t, 1H), 7.33–7.36 (m, 3H); MS (ESI) m/z 451.2 (M+Na)$^+$.

Example 30

The syntheses described in Example 30 is illustrated in SCHEME 8.

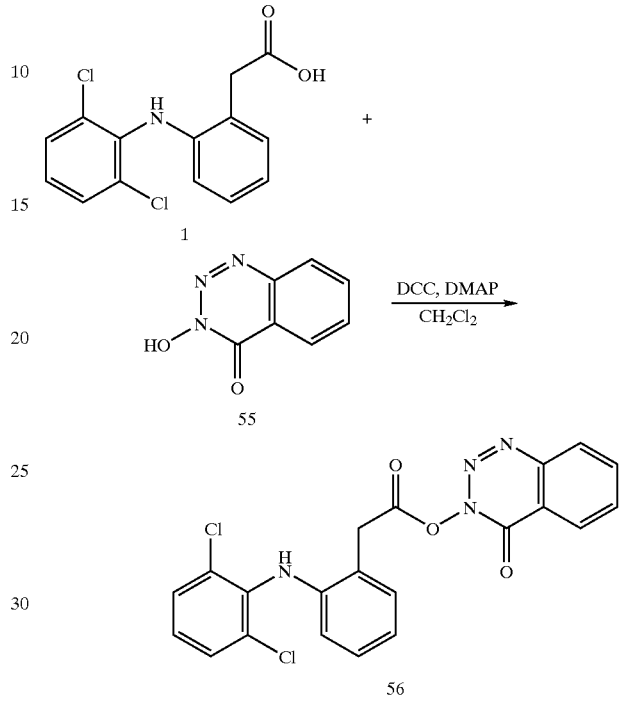

Compound 56 (Scheme 8). Compound 56 was synthesized from diclofenac (1) (0.89 g, 3 mmol), compound 55 (0.49 g, 3 mmol), DCC (0.62 g, 3 mmol) and DMAP (0.12 g, 1 mmol) employing the procedure described in Example 1. The compound was purified by column chromatography on a silica gel column using CH$_2$Cl$_2$ as an eluent to give 0.4 g (30%) of compound 56 as a pale yellow solid. $^1$H NMR (CDCl$_3$) δ 4.29 (s, 2H), 6.36 (br, 1H, ex D$_2$O), 6.64 (d, 1H), 6.98 (t, 1H), 7.78 (t, 1H), 7.21 (t, 1H), 7.32 (d, 2H), 7.42 (d, 1H), 7.85 (t, 1H), 8.01 (t, 1H), 8.24 (d, 1H), 8.38 (d, 1H); MS (ESI) m/z 431.8 (M+H)$^+$.

Examples 31–44

The syntheses of compounds 58–71 are described in Examples 31–44, respectively. The synthetic strategies employed are illustrated in SCHEME 9.

Scheme 9

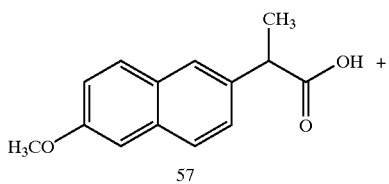

Scheme 9

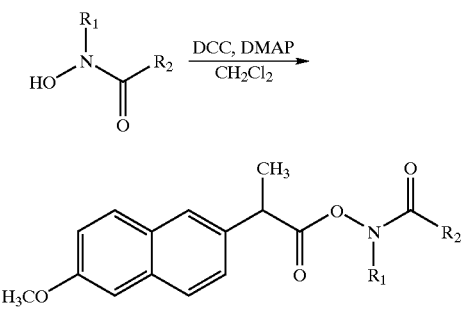

| | |
|---|---|
| 2. $R_1 = H, R_2 = CH_3$ | 58. $R_1 = H, R_2 = CH_3$ |
| 3. $R_1 = H, R_2 = OCH_2CH_3$ | 59. $R_1 = H, R_2 = OCH_2CH_3$ |
| 4. $R_1 = H, R_2 = C_6H_5$ | 60. $R_1 = H, R_2 = C_6H_5$ |
| 5. $R_1 = H, R_2 = OCH_2C_6H_5$ | 61. $R_1 = H, R_2 = OCH_2C_6H_5$ |
| 6. $R_1 = C_6H_5, R_2 = C_6H_5$ | 62. $R_1 = C_6H_5, R_2 = C_6H_5$ |
| 7. $R_1 = H, R_2 = C(CH_3)_2CH_2Cl$ | 63. $R_1 = H, R_2 = C(CH_3)_2CH_2Cl$ |
| 8. $R_1 = CH_3, R_2 = CH_2CH_3$ | 64. $R_1 = CH_3, R_2 = CH_2CH_3$ |
| 9. $R_1 = CH(CH_3)_2,$ $R_2 = CH(CH_3)_2$ | 65. $R_1 = CH(CH_3)_2,$ $R_2 = CH(CH_3)_2$ |
| 10. $R_1 = CH(CH_3)_2,$ $R_2 = CH_2CH_3$ | 66. $R_1 = CH(CH_3)_2,$ $R_2 = CH_2CH_3$ |
| 11. $R_1 = CH_3,$ $R_2 = CH_2SCH_3$ | 67. $R_1 = CH_3,$ $R_2 = CH_2SCH_3$ |
| 12. $R_1 = CH_3,$ $R_2 = CH_2SCH_2C_6H_5$ | 68. $R_1 = CH_3, R_2 = CH_2SO_2CH_3$ |
| | 69. $R_1 = CH_3, R_2 = CH_2SOCH_3$ |
| | 70. $R_1 = CH_3,$ $R_2 = CH_2SCH_2C_6H_5$ |
| | 71. $R_1 = CH_3,$ $R_2 = CH_2SO_2CH_2C_6H_5$ |

Compounds 58–71 (Scheme 9). Compounds 58–71 are synthesized as described above for the preparation of compounds 13–26, respectively, employing naproxen (57), DCC, DMAP and compounds 2–12 as starting materials. The compounds are purified by either crystallization or column chromatography.

Examples 45–58

The syntheses of compounds 72–85 are described in Examples 45–58, respectively. The synthetic strategies employed are illustrated in SCHEME 10.

Scheme 10

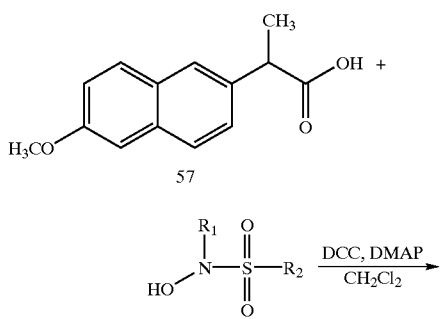

Scheme 10

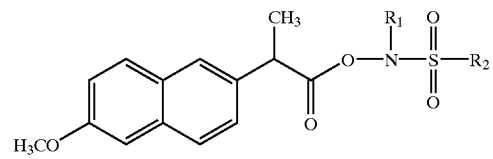

| | |
|---|---|
| 27. $R_1 = H, R_2 = p\text{-}C_6H_4CH_3$ | 72. $R_1 = H, R_2 = p\text{-}C_6H_4CH_3$ |
| 28. $R_1 = CH_3, R_2 = p\text{-}C_6H_4CH_3$ | 73. $R_1 = CH_3, R_2 = p\text{-}C_6H_4CH_3$ |
| 29. $R_1 = CH(CH_3)_2,$ $R_2 = p\text{-}C_6H_4CH_3$ | 74. $R_1 = CH(CH_3)_2, R_2 = p\text{-}C_6H_4CH_3$ |
| 30. $R_1 = CH_3,$ $R_2 = p\text{-}C_6H_4OCH_3$ | 75. $R_1 = CH_3, R_2 = p\text{-}C_6H_4OCH_3$ |
| 31. $R_1 = CH_3, R_2 = CH_3$ | 76. $R_1 = CH_3, R_2 = CH_3$ |
| 32. $R_1 = CH_3, R_2 = p\text{-}C_6H_4NO_2$ | 77. $R_1 = CH_3, R_2 = p\text{-}C_6H_4NO_2$ |
| 33. $R_1 = CH_3, R_2 = CH_2CH_3$ | 78. $R_1 = CH_3, R_2 = CH_2CH_3$ |
| 34. $R_1 = CH_3,$ $R_2 = m\text{-}C_6H_4CF_3$ | 79. $R_1 = CH_3, R_2 = m\text{-}C_6H_4CF_3$ |
| 35. $R_1 = CH_3,$ $R_2 = CH_2CH_2CH_3$ | 80. $R_1 = CH_3, R_2 = CH_2CH_2CH_2CH_3$ |
| 36. $R_1 = CH_3,$ $R_2 = 2,4,6\text{-}C_6H_2(CH_3)_3$ | 81. $R_1 = CH_3,$ $R_2 = 2,4,6\text{-}C_6H_2(CH_3)_3$ |
| 37. $R_1 = CH_3,$ $R_2 = CH_2CH_3$ | 82. $R_1 = CH_3, R_2 = CH_2CH_2CH_3$ |
| 38. $R_1 = H,$ $R_2 = 2,4,6\text{-}C_6H_2(CH_3)_3$ | 83. $R_1 = H, R_2 = 2,4,6\text{-}C_6H_2(CH_3)_3$ |
| | 84. $R_1 = CH_2CH_2CH_2SO_3Na,$ $R_2 = p\text{-}C_6H_4CH_3$ |
| | 85. $R_1 = CH_2CH_2CH_2CH_2SO_3Na,$ $R_2 = p\text{-}C_6H_4CH_3$ |

Compounds 72–85 (Scheme 10). Compounds 72–85 are synthesized as described above for the preparation of compounds 39–52, respectively, employing naproxen (57) and compounds 27–38 as starting materials. The compounds are purified by either column chromatography or crystallization.

Examples 59–72

The syntheses of compounds 87–100 are described in Examples 59–72, respectively. The synthetic strategies employed are illustrated in SCHEME 11.

Scheme 11

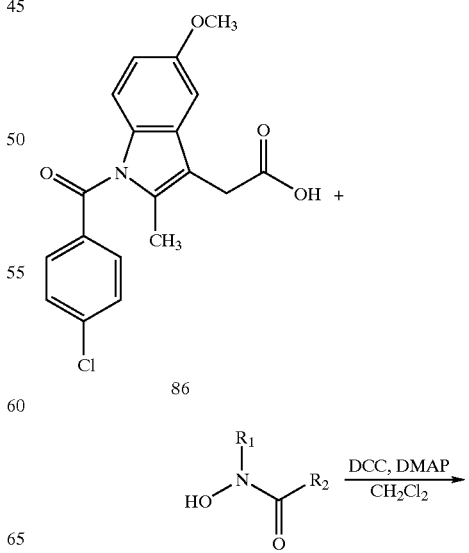

Scheme 11

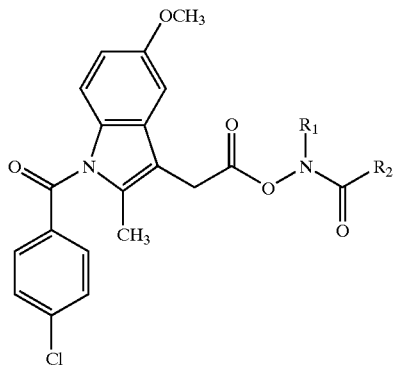

| | |
|---|---|
| 2. $R_1 = H, R_2 = CH_3$ | 87. $R_1 = H, R_2 = CH_3$ |
| 3. $R_1 = H, R_2 = OCH_2CH_3$ | 88. $R_1 = H, R_2 = OCH_2CH_3$ |
| 4. $R_1 = H, R_2 = C_6H_5$ | 89. $R_1 = H, R_2 = C_6H_5$ |
| 5. $R_1 = H, R_2 = OCH_2C_6H_5$ | 90. $R_1 = H, R_2 = OCH_2C_6H_5$ |
| 6. $R_1 = C_6H_5, R_2 = C_6H_5$ | 91. $R_1 = C_6H_5, R_2 = C_6H_5$ |
| 7. $R_1 = H,$ $R_2 = C(CH_3)_2CH_2Cl$ | 92. $R_1 = H,$ $R_2 = C(CH_3)_2CH_2Cl$ |
| 8. $R_1 = CH_3, R_2 = CH_2CH_3$ | 93. $R_1 = CH_3, R_2 = CH_2CH_3$ |
| 9. $R_1 = CH(CH_3)_2,$ $R_2 = CH(CH_3)_2$ | 94. $R_1 = CH(CH_3)_2,$ $R_2 = CH(CH_3)_2$ |
| 10. $R_1 = CH(CH_3)_2,$ $R_2 = CH_2CH_3$ | 95. $R_1 = CH(CH_3)_2,$ $R_2 = CH_2CH_3$ |
| 11. $R_1 = CH_3, R_2 = CH_2SCH_3$ | 96. $R_1 = CH_3, R_2 = CH_2SCH_3$ |
| 12. $R_1 = CH_3,$ $R_2 = CH_2SCH_2C_6H_5$ | 97. $R_1 = CH_3,$ $R_2 = CH_2SO_2CH_3$ |
| | 98. $R_1 = CH_3, R_2 = CH_2SOCH_3$ |
| | 99. $R_1 = CH_3, R_2 = CH_2SCH_2C_6H_5$ |
| | 100. $R_1 = CH_3,$ $R_2 = CH_2SO_2CH_2C_6H_5$ |

Compounds 87–100 (Scheme 11). Compounds 87–100 are synthesized as described above for the preparation of compounds 13–26, respectively, employing indomethacine (86), DCC, DMAP and compounds 2–12 as starting materials. The compounds are purified by either crystallization or column chromatography.

Examples 73–86

The syntheses of compounds 101–114 are described in Examples 73–86, respectively. The synthetic strategies employed are illustrated in SCHEME 12.

Scheme 12

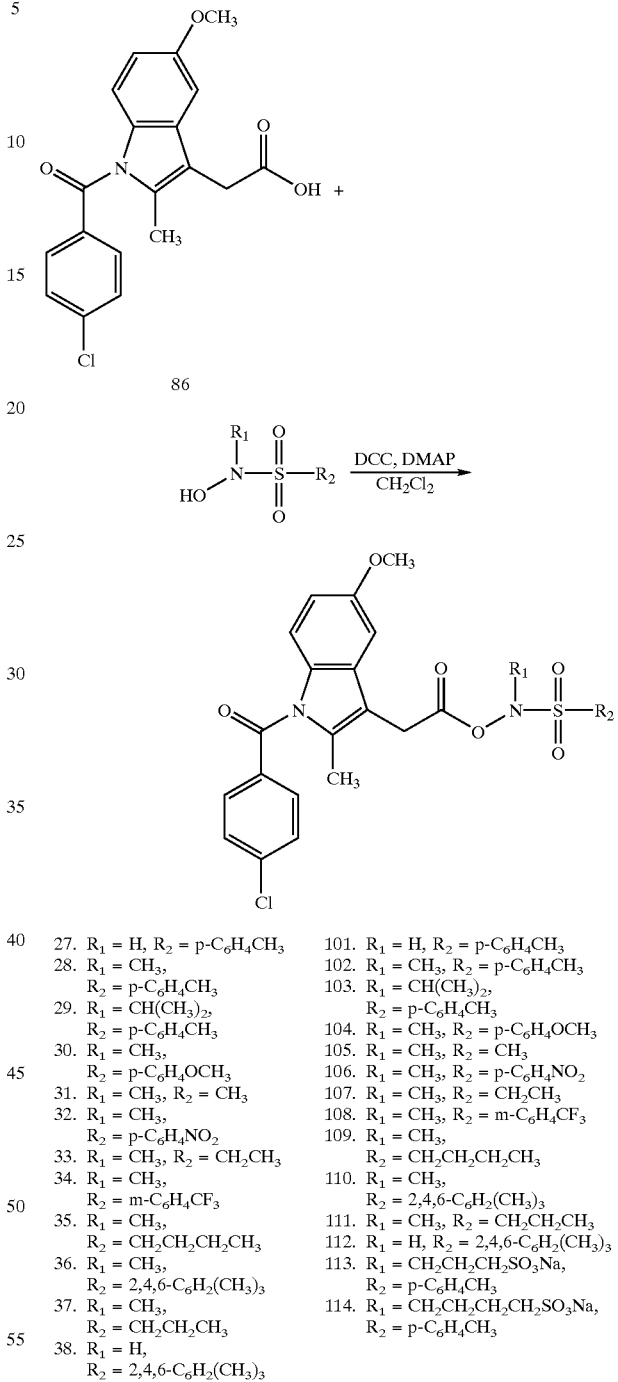

| | |
|---|---|
| 27. $R_1 = H, R_2 = p\text{-}C_6H_4CH_3$ | 101. $R_1 = H, R_2 = p\text{-}C_6H_4CH_3$ |
| 28. $R_1 = CH_3,$ $R_2 = p\text{-}C_6H_4CH_3$ | 102. $R_1 = CH_3, R_2 = p\text{-}C_6H_4CH_3$ |
| 29. $R_1 = CH(CH_3)_2,$ $R_2 = p\text{-}C_6H_4CH_3$ | 103. $R_1 = CH(CH_3)_2,$ $R_2 = p\text{-}C_6H_4CH_3$ |
| 30. $R_1 = CH_3,$ $R_2 = p\text{-}C_6H_4OCH_3$ | 104. $R_1 = CH_3, R_2 = p\text{-}C_6H_4OCH_3$ |
| 31. $R_1 = CH_3, R_2 = CH_3$ | 105. $R_1 = CH_3, R_2 = CH_3$ |
| 32. $R_1 = CH_3,$ $R_2 = p\text{-}C_6H_4NO_2$ | 106. $R_1 = CH_3, R_2 = p\text{-}C_6H_4NO_2$ |
| 33. $R_1 = CH_3, R_2 = CH_2CH_3$ | 107. $R_1 = CH_3, R_2 = CH_2CH_3$ |
| 34. $R_1 = CH_3,$ $R_2 = m\text{-}C_6H_4CF_3$ | 108. $R_1 = CH_3, R_2 = m\text{-}C_6H_4CF_3$ |
| 35. $R_1 = CH_3,$ $R_2 = CH_2CH_2CH_3$ | 109. $R_1 = CH_3,$ $R_2 = CH_2CH_2CH_2CH_3$ |
| 36. $R_1 = CH_3,$ $R_2 = 2,4,6\text{-}C_6H_2(CH_3)_3$ | 110. $R_1 = CH_3,$ $R_2 = 2,4,6\text{-}C_6H_2(CH_3)_3$ |
| 37. $R_1 = CH_3,$ $R_2 = CH_2CH_2CH_3$ | 111. $R_1 = CH_3, R_2 = CH_2CH_2CH_3$ |
| 38. $R_1 = H,$ $R_2 = 2,4,6\text{-}C_6H_2(CH_3)_3$ | 112. $R_1 = H, R_2 = 2,4,6\text{-}C_6H_2(CH_3)_3$ |
| | 113. $R_1 = CH_2CH_2CH_2SO_3Na,$ $R_2 = p\text{-}C_6H_4CH_3$ |
| | 114. $R_1 = CH_2CH_2CH_2CH_2SO_3Na,$ $R_2 = p\text{-}C_6H_4CH_3$ |

Compounds 101–114 (Scheme 12). Compounds 101–114 are synthesized as described above for the preparation of compounds 39–52, respectively, employing indomethacine (86) and compounds 27–38 as starting materials. The compounds are purified by either column chromatography or crystallization.

Example 87

An invention compound, Compound 54 (a pro-drug of Diclofenac), was evaluated for its safety profile in rat models of gastropathy and enteropathy. Compound 54 exhibited significantly less gastric lesion formation and ulcer formation than equivalent doses of Diclofenac. In adjuvant-induced arthritis model, compound 54 exhibited equivalent efficacy to equimolar doses of Diclofenac.

Gastropathy: Male Sprague-Dawley rats (150–174 g) were obtained from Harlan (San Diego, Calif.). Animals were allowed to acclimatize to the facility for a minimum of 3 days and provided food and water ad libitium until the day before the study. Rats were fasted for 18 hours prior to the study. Diclofenac sodium salt was formulated in PBS, and dosed at 5 ml/kg, and Compound 54 was formulated in polyethyleneglycol (PEG )(MW. 300; Sigma Chemical Co., St. Louis, Mo.), and dosed at 1 ml/kg. Drugs were administered orally as a single dose in the morning and water removed. Two and one-half hours after dosing, rats were injected with 1 ml of 10 mg/ml Evans Blue solution and sacrificed 30 minutes later. Stomachs were removed, placed in weigh boats containing cold PBS, and re-coded with letters to blind the observer. Stomachs were then opened along the greater curvature, any contents removed and then placed flat with the lumen facing up to score blue-stained lesions for gastric toxicity according to the following criteria: First, the number of small rounded lesions were counted followed by measurement of total length of linear lesions of greater than or equal to 2 mm. The two numbers obtained (round lesion number and linear length) were added together to give a total gastropathy score expressed as Total Gastric Lesions.

FIG. 1 illustrates the total length of intestinal ulcers measured for rats treated with vehicle, diclofenac or equimolar invention compound 54. Diclofenac caused substantial ulceration, while compound 54 had no ulcerogenic effect, just like the vehicle PEG.

Enteropathy: Male Sprague-Dawley rats (150–174 g) were obtained from Harlan. Animals were allowed to acclimatize to the facility for a minimum of 3 days and provided with food and water ad libitium. Diclofenac sodium salt was formulated in PBS, and dosed at 5 ml/kg, and compound 54 was formulated in polyethyleneglycol (MW. 300; Sigma Chemical Co.), dosed at 1 ml/kg. Drugs were administered orally either as a single dose (late morning) or twice daily between 8:00–10:00 and 4:00–5:00 beginning with a morning dose for a total of three days. Groups contained 6–8 animals per treatment. On the fourth day each rat was injected intravenously with 1 ml of a 10 mg/ml solution of Evan's Blue to stain the damaged blood vessels in intestinal erosions and ulcers. Animals were sacrificed 10 to 20 minutes after administration of Evan's Blue. The small intestine was then removed from each rat and placed in a large weigh boat in cold PBS, stored briefly in a refrigerator until boats were re-coded to blind the observer. Each intestinal segment was then opened longitudinally and, using a fiber optic light, scored for erosions and ulceration according to the following criteria:

Erosions: An erosion is a shallow lesion that does not penetrate past the muscularis mucosa immediately below the epithelium. After Evan's Blue injection, intestinal lesions are seen as shallow lesions that are moderately stained around the edge, but with little to no staining in the middle. The depth of an erosion is sometimes only detectable when the edge of the tissue is lifted to reflect light at a different angle. Erosions are usually small and round or oval, but are sometimes as much as 1–2 mm wide, and as long as 1–2 cm, running along the area of mesenteric attachment. When erosions are elongated, the length is measured in mm and divided by 2; otherwise, the erosions are merely counted individually. Note that some areas of intestinal tissue stain blue, but are not erosions. These tend to be near the mesenteric membrane attachment sites and may represent areas of increased permeability that have not progressed to the extent that cell loss has occurred. When such areas are viewed while lifting the edge of the tissue, there is no clear depression in the center, and often the mesentery below contributes significantly to the observed staining.

Ulcers: An ulcer is a deep lesion penetrating the muscularis mucosa. It is usually thickened and inflamed. After Evan's Blue injection, ulcers present several different types of appearance. Small ulcers are round and oval, thickened and darkly stained (including the center), often with a small white scab on top. Larger ulcers are usually linear, running along the area where the mesenteric membrane attaches. The resulting trough can either be deep (e.g., ~1 mm) and empty, or filled with granulation tissue. The surrounding intestine is almost always thickened and inflamed. All ulcers are quantified by measuring their long dimensions in mm.

Figure 2:
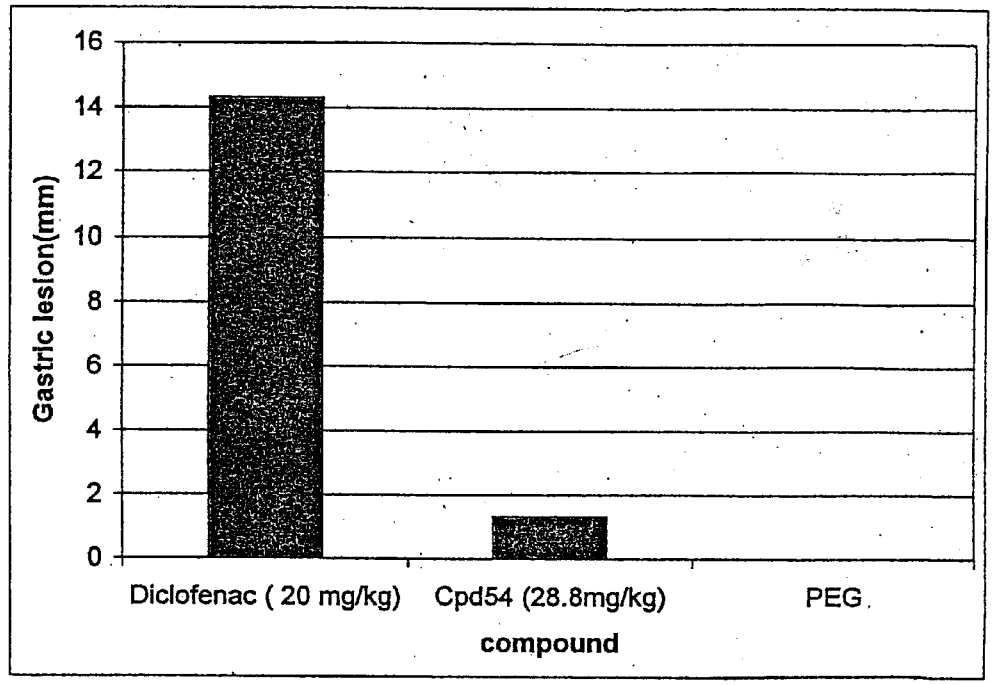
FIG. 2 illustrates the total length of gastric lesion measured for rats treated with vehicle, diclofenac or equimolar invention compound 54.

FIG. 2 illustrates the total length of gastric lesion measured for rats treated with vehicle, diclofenac or equimolar invention compound 54. Compound 54 caused 73% less lesion than did an equimolar dose of diclofenac.

Adjuvant-induced Arthritis: Male Lewis rats (175–199 g) were obtained from Harlan San Diego, Calif.). Animals were allowed to acclimatize to the facility for a minimum of 3 days and provided food and water ad libitium. Mycobacterium tuberculosis (Difco, Bacto H37 RA 3114–25) was dissolved in mineral oil (5 mg/ml) and arthritis induced by injecting 100 µl of the solution into the left footpad using a 25 G needle. Paw volume was measured using a water plethysmometer (UBS Basile, Stoelting Co.). A line was drawn across the right ankle to provide the level for baseline measurement of paw volume and paw volume was measured on days 0, 5, 11, 13 and 15. Data is expressed as percent inhibition paw swelling on day 15 which is calculated as follows: % inhibition=$(1-((Vol_{drug-teated\ day\ 15}-Vol_{drug-treated\ day\ 5})/(Vol_{vehicle\ treated\ day\ 15}-Vol_{vehicle-treated\ day\ 5})))\times 100$. Diclofenac sodium salt was formulated in PBS, and dosed at 5 ml/kg, and Compound 54 was formulated in polyethyleneglycol (MW. 300; Sigma Chemical Co., St. Louis, Mo.), and dosed at 1 ml/kg. Diclofenac, compound 54 and vehicle were administered orally, daily, on days 8–15.

Figure 3:
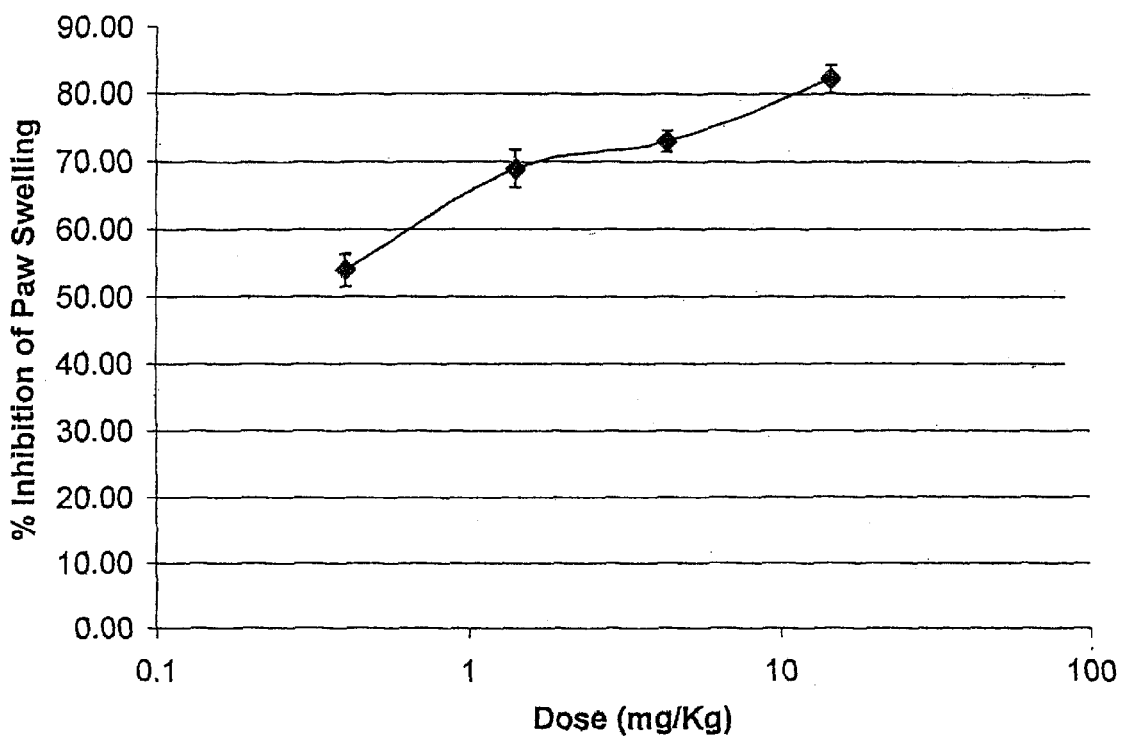
FIG. 3 illustrates the inhibition of paw volume increase in the uninjected feet of Lewis rats in which arthritis was induced by injection of adjuvant into the footpad.

FIG. 3 illustrates the inhibition of paw volume increase in the uninjected feet of Lewis rats in which arthritis was induced by injection of adjuvant into the, footpad. Invention compound 54 displayed anti-inflammatory activity similar to diclofenac in the chronicadjuvant arthritis model.

It will be apparent to those skilled in the art that various changes may be made in the invention without departing from the spirit and scope thereof, and therefore, the invention encompasses embodiments in addition to those specifically disclosed in the specification, but only as indicated in the appended claims.

What is claimed is:

1. A compound having the structure:

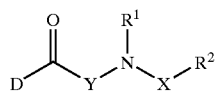

wherein:
X is C(O), C(O)O, S(O), S(O)$_2$, C(S), C(O)S, C(S)S, or C(S)O;
Y is O or S;
$R^1$ and $R^2$ are each independently hydrogen, hydrocarbyl, substituted hydrocarbyl, alkoxy, substituted alkoxy, aryloxy, substituted aryloxy, heterocyclic, or substituted heterocyclic; or $R^1$ and $R^2$ together with N and X can form a cyclic moiety; and
D—C(O)— is derived from a non-steroidal anti-inflammatory drug bearing a free carboxyl group.

2. A compound according to claim 1, wherein X is C(O) or S(O)$_2$.

3. A compound according to claim 1, wherein Y is O.

4. A compound according to claim 1, wherein $R^1$ and $R^2$ are each independently alkyl, substituted alkyl, aryl, substituted aryl, alkoxy, or substituted alkoxy.

5. A compound according to claim 1, wherein the substituents on $R^1$ and/or $R^2$, when optionally substituted, are optionally substituted alkyl, optionally substituted cycloalkyl, optionally substituted heterocyclic, optionally substituted aryl, optionally substituted heteroaryl, optionally substituted aryloxy, optionally substituted alkoxy, thioalkyl, hydroxyl, mercapto, alkylthio, alkylthioalkyl, halogen, trihalomethyl, cyano, nitro, nitrone, —C(O)H, carboxyl, alkyoxycarbonyl, carbamate, sulfonyl, alkylsulfonyl, alkylsulfonylalkyl, sulfinyl, alkylsulfinyl, alkylsulfinylalkyl, sulfonamide, sulfuryl, amino, alkylamino, arylamino, aminosulfonyl, alkylaminosulfonyl, dialkylaminosulfonyl, amido, alkoxycarbonyl, acyl, oxyacyl —SO$_3$M wherein M is H$^+$, Li$^+$, Na$^+$, K$^+$, or NH$_4{}^+$, or —PO$_3$M wherein M is as defined above; or —OC(S)NR$^3$, —OC(O)NR$^3$, —C(S)NR$^3$, —NR$^3$C(S)R$^3$, —NR$^3$C(S)NR$_3$, —OC(S)NR$^3$, —NR$^3$C(S)OR$^3$, —C(S)OR$^3$, —OC(S)R$^3$, or —OC(S)OR$^3$, wherein R$^3$ is independently any of the substituent, contemplated for $R^1$ and $R^2$ as defined herein.

6. A compound according to claim 1, wherein said NSAID) is diclofenac, naproxen, indomethacine, acetylsalicylic acid, flubiprofen, sulindac, ibuprofen, benoxaprofen, benzofenac, bucloxic acid, butibufen, carprofen, cicloprofen, cinmetacin, clidenac, clopirac, etodolac, fenbufen, fenclofenac, fenclorac, fenoprofen, fentiazac, flunoxaprofen, furaprofen, furobufen, furafenac, ibufenac, indoprofen, isoxepac, ketoprofen, Ionazolac, metiazinic, mefenamic acid, meclofenmic acid, piromidic acid, salsalate, miroprofen, oxaprozin, oxepinac, pirprofen, pirozolac, protizinic acid, suprofen, tiaprofenic acid, tolmetin, or zomepirac.

7. A compound according to claim 6, wherein said NSAID is diclolfenac, naproxen, indomethacine, acetylsalicylic acid, flubiprofen, sulindac, or ibuprofen.

8. A formulation comprising a compound according to claim 1, in a pharmaceutically acceptable carrier therefor.

9. A formulation according to claim 8, wherein the pharmaceutically acceptable carrier is a solid, solution, emulsion, dispersion, micelle, or liposome.

10. A formulation according to claim 9, wherein the pharmaceutically acceptable carrier further comprises an enteric coating.

11. A method for treating inflammation and inflammation-related conditions, said method comprising administering to a subject in need thereof an effective amount of a compound according to claim 1.

12. A method according to claim 11, wherein the inflammation-related condition is arthritis.

13. A method according to claim 12, wherein the arthritis is rheumatoid arthritis, gouty arthritis, osteoarthritis, juvenile arthritis, systemic lupus erythematosus, or spondyloarthopathies.

14. A method according to claim 11, wherein the inflammation-related condition is a gastrointestinal condition, a headache, asthma, bronchitis, menstrual cramps, tendinitis, or bursitis.

15. A method according to claim 11, wherein the inflammation-related condition is a gastrointestinal condition.

16. A method according to claim 15, wherein the gastrointestinal condition is inflammatory bowel disease, Crohn's disease, gastritis, irritable bowel syndrome, or ulcerative colitis.

17. A method according to claim 11, wherein the inflammation-related condition is a headache.

18. A method according to claim 17, wherein the headache is a migraine.

19. A method according to claim 11, wherein the inflammation-related condition is associated with vascular diseases, periarteritis nodosa, thyroidiris, aplastic anemia, Hodgkin's disease, sclerodoma, rheumatic fever, type I diabetes, myasthenia gravis, colorectal cancer, sarcoidosis, nephrotic syndrome, Behcet's syndrome, potymyositis, gingivitis, hypersensitivity, conjunctivitis, swelling occurring after injury, or myocardial ischemia.

20. A method for the preparation of a NSAID prodrug with reduced GI side effect(s), said method comprising covalently linking said NSAID to a hydroxamate.

21. A method for the preparation of a dual inhibitor of cyclooxygenase and 5-lipoxygenase, wherein said dual inhibitor has reduced GI side effect(s) and/or enhanced activity, said method comprising covalently linking an NSAID to a hydroxamate.

22. A method for the preparation of a compound which is both a promoter of apoptosis and an inhibitor of matrix metalloproteinase with reduced GI side effect(s), said method comprising covalently linking an NSAID to a hydroxamate.

23. A method for reducing side effects associated with anti-inflammatory agents, said method comprising administering to a subject in need thereof an effective amount of a compound according to claim 1.

24. A method according to claim 23, wherein the subject is human.

25. A method for reducing side effects associated with anti-inflammatory agents and enhancing the anti-inflammatory activity, said method comprising administering to a subject in need thereof an effective amount of a compound according to claim 1.

26. A method according to claim 25, wherein the subject is human.

27. A method for treatment of cancer and/or tumor by promoting apoptosis in a subject with reduced GI side effect, said method comprising administering to the subject an effective amount of a compound according to claim 1.

28. A method according to claim 27, wherein the subject is human.

29. A method for treatment of cancer and/or tumor by inhibiting matrix metalloproteinase, said method comprising administering to the subject an effective amount of a compound according to claim 1.

30. A method according to claim 29, wherein the subject is human.

31. A method for treatment of cancer and/or tumor by both promoting apoptosis and inhibiting matrix metalloproteinases in a subject with reduced GI side effect, said method comprising administering to the subject an effective amount of a compound according to claim 1.

32. A method according to claim 31, wherein the subject is human.

33. A method of inhibiting the proliferation of a hyperproliferative mammalian cell in a subject in need thereof, said method comprising administering to the subject an effective amount of a compound according to claim 1.

34. A method according to claim 33, wherein the subject is human.

35. A method for the dual inhibition of cyclooxygenase and 5-lipoxygenase in a subject in need thereof, said method comprising administering to the subject an effective amount of a compound according to claim 1.

36. A method according to claim 35, wherein the subject is human.

\* \* \* \* \*